United States Patent
Ohishi

(10) Patent No.: US 8,891,843 B2
(45) Date of Patent: Nov. 18, 2014

(54) MEDICAL IMAGE DIAGNOSIS APPARATUS

(75) Inventor: Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 185 days.

(21) Appl. No.: 13/641,717

(22) PCT Filed: Aug. 17, 2011

(86) PCT No.: PCT/JP2011/004606
§ 371 (c)(1),
(2), (4) Date: Oct. 17, 2012

(87) PCT Pub. No.: WO2012/023283
PCT Pub. Date: Feb. 23, 2012

(65) Prior Publication Data
US 2013/0034283 A1    Feb. 7, 2013

(30) Foreign Application Priority Data

Aug. 17, 2010  (JP) ................. 2010-182099
Aug. 17, 2011  (JP) ................. 2011-178359

(51) Int. Cl.
G06K 9/00     (2006.01)
A61B 6/00     (2006.01)
A61B 6/12     (2006.01)
A61B 6/03     (2006.01)
G06T 5/50     (2006.01)

(52) U.S. Cl.
CPC ............. *A61B 6/487* (2013.01); *A61B 6/5258* (2013.01); *A61B 6/481* (2013.01); *A61B 6/504* (2013.01); *G06T 2207/30021* (2013.01); *A61B 6/12* (2013.01); *A61B 6/466* (2013.01); *G06T 2207/10121* (2013.01); *G06T 2207/30101* (2013.01); *A61B 6/032* (2013.01); *G06T 5/50* (2013.01); *G06T 2207/10081* (2013.01); *A61B 6/5211* (2013.01)
USPC ............ 382/128; 382/130; 382/131; 382/132

(58) Field of Classification Search
None
See application file for complete search history.

(56) References Cited

U.S. PATENT DOCUMENTS 5,285,786 A * 2/1994 Fujii ............................ 600/425
7,751,523 B2 * 7/2010 Ohishi ............................ 378/4
(Continued)

FOREIGN PATENT DOCUMENTS

CN   101422370 A   5/2009
CN   101442934 A   5/2009
(Continued)

OTHER PUBLICATIONS

Office Action issued Oct. 8, 2013 in Chinese Patent Application No. 201180002670.1.
(Continued)

*Primary Examiner* — Anand Bhatnagar
*Assistant Examiner* — Soo Park
(74) *Attorney, Agent, or Firm* — Oblon, Spivak, McClelland, Maier & Neustadt, L.L.P.

(57) ABSTRACT

According to one embodiment, a medical image diagnosis apparatus includes a volume rendering image generation part, mask image-storage, real time fluoroscopic image generation part, subtraction image generation part, coil image generation part, and image composition part. The volume rendering image generation part generates, from volume data, a volume rendering image representing blood vessel information. The mask image-storage stores fluoroscopic mask images. The real time fluoroscopic image generation part acquires real time fluoroscopic images for each chronological sequence accompanying device insertion. The subtraction image generation part generates a subtraction image by subtraction processing on the fluoroscopic mask image stored in the mask image storage and the real time fluoroscopic image acquired for each chronological sequence. The coil image generation part generates a coil image from the fluoroscopic mask image. The image composition part generates a composite image of the volume rendering image, the subtraction image, and the coil image.

8 Claims, 11 Drawing Sheets

(56) References Cited

U.S. PATENT DOCUMENTS

| | | | |
|---|---|---|---|
| 8,090,427 B2 * | 1/2012 | Eck et al. | 600/425 |
| 8,463,007 B2 * | 6/2013 | Steinberg et al. | 382/128 |
| 8,488,853 B2 * | 7/2013 | Sato et al. | 382/128 |
| 8,542,902 B2 * | 9/2013 | Ohishi | 382/131 |
| 2009/0022262 A1 | 1/2009 | Ohishi | |
| 2009/0123046 A1 | 5/2009 | Mielekamp et al. | |
| 2009/0192385 A1 * | 7/2009 | Meissner et al. | 600/426 |
| 2010/0208973 A1 * | 8/2010 | Lienard et al. | 382/132 |
| 2011/0103666 A1 | 5/2011 | Ohishi | |

FOREIGN PATENT DOCUMENTS

| | | |
|---|---|---|
| JP | 2003-290189 A | 10/2003 |
| JP | 2009 39521 | 2/2009 |
| JP | 2009 536543 | 10/2009 |
| JP | 2011 115562 | 6/2011 |

OTHER PUBLICATIONS

Kiura, Y., et al., "Efficacy of Fusion CTA for Following Aneurysms Treated by Coil Emobilization," Progress in Cl, vol. 30, No. 1, pp. 29-34, (Jun. 30, 2008) (with English abstract).

International Search Report Issued Nov. 1, 2011 in PCT/JP11/04606 Filed Aug. 17, 2011.

* cited by examiner

MEDICAL IMAGE DIAGNOSIS APPARATUS

CROSS-REFERENCE TO RELATED APPLICATIONS

This application is based upon and claims the benefit of priority from Japanese Patent Applications No. 2010-182099, filed Aug. 17, 2010 and No. 2011-178359, filed Aug. 17, 2011; the entire contents of all of which are incorporated herein by reference.

TECHNICAL FIELD

An embodiment of the present invention relates to a medical image diagnosis apparatus.

BACKGROUND ART

Medical image technologies using an X-ray diagnosis device, etc. are rapidly progressing. In intervention treatment (intravascular treatment), etc. which is one treatment method for aneurysms, for example, a doctor guides a catheter inserted from the groin, etc. to a lesion part using a guide wire that has been inserted inside the catheter.

Subsequently, from the tip end of the catheter, an embolization substance such as a coil is placed in the aneurysm. By placing the coil therein, blood flow is blocked and, as a result, blood is coagulated within the aneurysm for treatment. In this case, it is possible to visually recognize a blood vessel in an X-ray fluoroscopic image by injecting a contrast agent.

On the other hand, if the contrast agent is continuously injected, there is a problem of putting an excessive load onto the patient. For this, a two-dimensional road map displayed by overlapping an X-ray image captured while once running the contrast agent and a real time X-ray fluoroscopic image, is used.

However, it is necessary to recreate the two-dimensional road map due to bed movement, changes in imaging directions, patient movement, etc. Complicated recreation of the two-dimensional road map is problematic in that it leads to an increase in the examination time as well as an increase in the usage amount of the contrast agent.

In order to solve such a problem, a three-dimensional road map that is a road map image created using a volume rendering image and is displayed and overlapping with a real time fluoroscopic image, is expected to have an effect in reducing the examination time as well as the amount of the contrast agent.

However, in the three-dimensional road map displayed by overlapping a real time fluoroscopic image and a volume rendering image, because devices such as a guide wire, catheter, etc. and human tissue structures such as bones are displayed in an overlapping manner, there is a problem in that device images are very difficult to see.

In order to improve the readability of the image of a device, a technology of extracting device information as a result of a subtraction process of a real time fluoroscopic image and a fluoroscopic mask image and overlapping the device information with a volume rendering image is known. However, in this technology, when an imaging angle is changed, because a coil is also present in a fluoroscopic mask image to be newly regenerated, there is a problem in that a coil that has already been placed therein cannot be displayed.

DETAILED DESCRIPTION

According to one embodiment, a medical image diagnosis apparatus includes a volume rendering image generation part, mask image-storage, real time fluoroscopic image generation part, subtraction image generation part, coil image generation part, and image composition part. The volume rendering image generation part generates, from volume data, a volume rendering image that represents blood vessel information inside a subject. The mask image-storage stores fluoroscopic mask images. The real time fluoroscopic image generation part acquires real time fluoroscopic images for each chronological sequence accompanying device insertion. The subtraction image generation part generates a subtraction image by subtraction processing on the fluoroscopic mask image stored in the mask image storage and the real time fluoroscopic image acquired for each chronological sequence. The coil image generation part generates a coil image from the fluoroscopic mask image. The image composition part generates a composite image of the volume rendering image, the subtraction image, and the coil image.

With reference to FIG. 1 to 11, an X-ray imaging apparatus according to Embodiment 1 to Embodiment 3 is described.

[Embodiment 1]
(Outline of the Operation)

Figure 1:
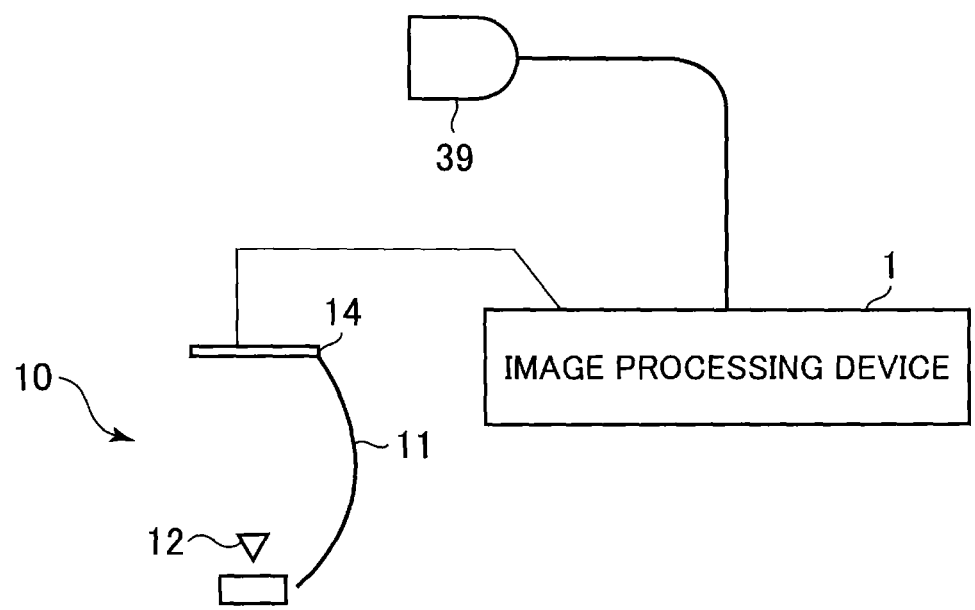
FIG. 1 is a schematic block diagram showing the configuration of an X-ray imaging apparatus according to Embodiment 1.

First, with reference to FIG. 1, the outline of the operation of an image processing device 1 and an X-ray imaging mechanism 10 related to Embodiment 1 is described. FIG. 1 is a schematic block diagram showing the configuration of the X-ray imaging apparatus related to Embodiment 1. The X-ray imaging mechanism 10 shown in FIG. 1 acquires volume data (three-dimensional vascular image data), as one example, as described below. The volume data is data for generating a volume rendering image V.

The X-ray imaging apparatus related to Embodiment 1 acquires a plurality of frames of projection data of two-dimensional mask images while causing the X-ray imaging mechanism 10 to rotate around a subject at a high speed. Next, the plurality of frames of projection data of the two-dimensional contrast images are acquired while rotating the X-ray imaging mechanism 10 again around the subject into which a contrast agent has been injected.

A mask image acquired at a certain angle and a contrast image acquired at the same angle are subjected to subtraction processing. DSA (Digital Subtraction Angiography) data is obtained by this subtraction processing.

Next, the DSA data is reconstructed to obtain volume data in which a vascular image is enhanced. The reconstructed volume data is stored in a three-dimensional image memory.

Next, the X-ray imaging apparatus generates a volume rendering image V, for example, as described below. Furthermore, a composite image of the volume rendering image V and a fluoroscopic subtraction image is generated.

The X-ray imaging apparatus starts fluoroscopic imaging based on an operation by a user. After starting fluoroscopic imaging, the X-ray imaging apparatus acquires fluoroscopic mask image data. Furthermore, the X-ray imaging apparatus acquires real time fluoroscopic image data. Moreover, the X-ray imaging apparatus generates fluoroscopic subtraction data by subtraction processing. Along with these processes, (1) the X-ray imaging apparatus enhances and displays a guide wire, catheter, etc. in the subject. Furthermore, (2) it is determined whether or not a command is received to generate a 3D road map. Moreover, (3) it is determined whether or not there are condition changes in imaging. Hereinafter, the outline of processes (1) to (3) is described.

(1) After starting the fluoroscopic imaging, a device such as a guide wire, catheter, etc. is inserted into the subject by a doctor while using fluoroscopic images as references. Then, the image processing device 1 performs detection processing, etc. on a line component with respect to the fluoroscopic subtraction data. As a result, other portions except those showing devices such as the guide wire, catheter, etc. in the fluoroscopic subtraction data, that is, noise, are suppressed. Consequently, in the fluoroscopic subtraction data, portions showing devices are displayed as relatively enhanced in comparison to the other portions.

(2) The X-ray imaging apparatus determines whether or not a command has been received to generate a 3D road map, for example, after inserting a device into the subject. The command is based on an operation by a doctor etc. If a command for generation is received, the X-ray imaging apparatus obtains volume data from the three-dimensional image memory. Furthermore, the X-ray imaging apparatus generates a volume rendering image V by performing a process such as volume rendering, etc. on the volume data. The process of volume rendering, etc. is, for example, executed according to the state indicated by information regarding the angle, field of vision, magnification rate, position, etc. of observation.

Furthermore, the X-ray imaging apparatus generates and displays a 3D road map image based on the fluoroscopic subtraction data of the above (1) and the volume rendering image, etc. of (2).

(3) The X-ray imaging apparatus determines whether or not there are any changes in conditions for imaging due to the observation angle, the magnification rate, the shifts of the bed, movement of the patient, etc. Furthermore, it is determined whether or not a command has been received to regenerate a fluoroscopic mask image M. If determined that there were the changes in the conditions or the command has been given, the X-ray imaging apparatus obtains volume data and regenerates the volume rendering image V in accordance with the condition changes. Moreover, the X-ray imaging apparatus generates a fluoroscopic mask image M and a real time fluoroscopic image R according to the condition changes.

Figure 2:
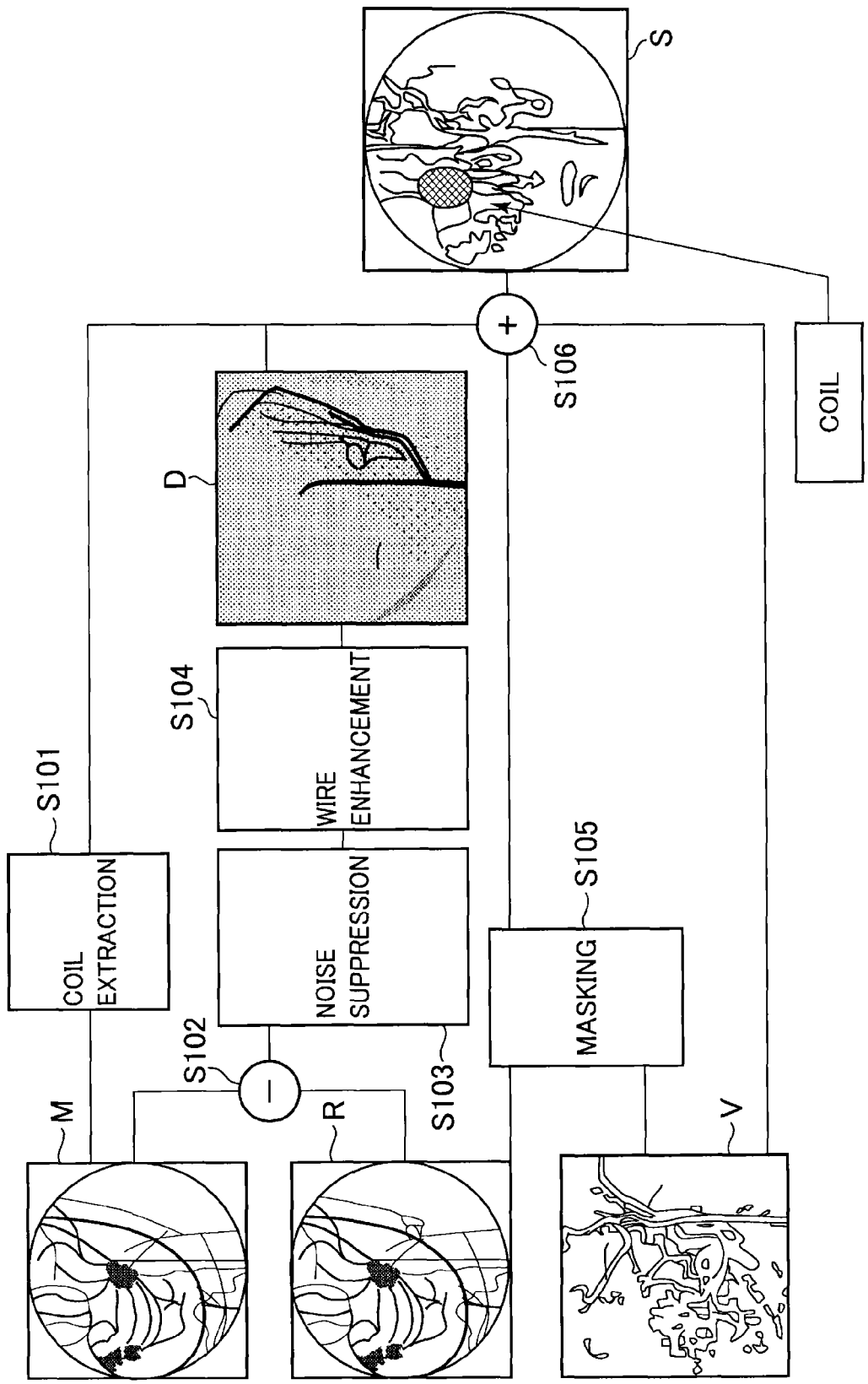
FIG. 2 is a schematic block diagram schematically showing the steps to generate a 3D road map image by the X-ray imaging apparatus of Embodiment 1.

Next, with reference to FIG. 2, the operation outline of the image processing device 1 in accordance with the condition changes in imaging or the command to regenerate a fluoroscopic mask image M is described. It should be noted that the operation is an example of coil embolization with respect to aneurysms.

<<Generation of Coil-Extracted Images>>

As shown in FIG. 2, when there are condition changes in imaging or a command is given to regenerate a fluoroscopic mask image M, the X-ray imaging mechanism 10 reobtains a fluoroscopic mask image M as well as a real time fluoroscopic image R. Furthermore, a coil is extracted from the reobtained fluoroscopic mask image M to generate a coil-extracted image C (S101).

<<Generation of Device-Enhanced Images>>

The image processing device 1 obtains fluoroscopic subtraction data by subtraction processing on the fluoroscopic mask image M and the real time fluoroscopic image R that are reobtained (S102). In FIG. 2, a symbol "−" displayed between the real time fluoroscopic image R and the fluoroscopic mask image M means subtraction processing. Furthermore, the image processing device 1 performs noise suppression processing on the fluoroscopic subtraction data (S103).

The image processing device 1 performs detection processing of a line component, etc. (enhancement of a wire) on the fluoroscopic subtraction data subjected to noise suppression processing. As a result, a device-enhanced image D in which a device such as a guide wire, etc. is relatively enhanced in the fluoroscopic image, is generated (S104).

<<Masking Processing>>

The image processing device 1 performs masking processing on the real time fluoroscopic image R. For example, the image processing device 1 performs a process to lower the composition ratio of the real time fluoroscopic image R only with respect to a superposed portion of the real time fluoroscopic image R and a portion at which a blood vessel in the volume rendering image V is present. Due to this process, even if the composition ratio of the real time fluoroscopic image R is increased, it is possible to avoid deterioration of the readability of the volume rendering image V (S105).

<<3D Roadmap Image>>

Composition processing of the coil-extracted image C, the device-enhanced image D, and the real time fluoroscopic image R subjected to masking processing is performed by the image processing device 1 (Step S106). Furthermore, the volume rendering image V and the image data subjected to the composition processing are further subjected to composition processing to generate a 3D road map image S. Moreover, the image processing device 1 causes the display 39 to display the 3D road map image S.

As described, the X-ray imaging apparatus related to Embodiment 1 composes and displays a real time fluoroscopic image R, a volume rendering image V, and a device-enhanced image D, etc. Thereby, it becomes possible for the user to grasp the positional relationship of blood vessels and the structure inside the subject. Consequently, it is possible for the user to grasp the relative positional changes of the subject and an imaging mechanism in the event of displacement. Furthermore, if there are condition changes in imaging or a command to regenerate a fluoroscopic mask image M is given, the X-ray imaging mechanism 10 recaptures the fluoroscopic mask image M as well as the real time fluoroscopic image R. Moreover, a coil-extracted image C is generated.

Therefore, when a 3D road map image S is newly generated, a situation of losing the coil in an image may be avoided.

(Entire Configuration of X-ray imaging apparatus)

Next, with reference to FIG. 1, the configuration of the X-ray imaging apparatus related to Embodiment 1 is described. As shown in FIG. 1, the X-ray imaging apparatus related to Embodiment 1 is configured including an X-ray imaging mechanism 10, an image processing device 1, and a display 39. Furthermore, the X-ray imaging apparatus comprises a system control part (not illustrated).

The system control part that is not illustrated controls the entire X-ray imaging apparatus such as the image processing device 1 and the X-ray imaging mechanism 10, etc.

An input device 28 includes, for example, a keyboard, a mouse and further, a road map switch. The road map switch is for inputting a command to compose a road map of blood vessels (3D road map image S) with respect to a current fluoroscopic image.

The display 39 receives each image data from the image processing device 1 and displays a fluoroscopic image, a device-enhanced image D, a 3D road map image S, etc.

(Configuration of X-ray Imaging Mechanism)

Next, with reference to FIG. 1, the configuration of the X-ray imaging mechanism 10 related to Embodiment 1 is described. The X-ray imaging mechanism 10 comprises a system control part, a mechanism control part, a bed, and an X-ray high voltage generator that are not illustrated. The X-ray high voltage generator that is not illustrated comprises an X-ray control part and a high voltage generation part. Furthermore, the X-ray imaging mechanism 10 comprises an X-ray source device that is not illustrated, an arm 11, and an X-ray detector 14. The X-ray source device comprises an X-ray tube 12 and an X-ray diaphragm (not illustrated).

The arm 11 supports the X-ray source device (X-ray tube 12) as well as the X-ray detector 14. For example, the C-shaped arm 11 rotates like a propeller at a high speed by a motor mounted on a base. The bed is for a subject to lie upon. The bed is controlled by the mechanism control part and allows a subject to be moved while remaining in place thereon.

The X-ray tube 12 uses high voltage power supplied by the X-ray high voltage generator to generate X-rays. The X-ray diaphragm device controls an irradiating field by blocking part of the X-rays generated by the X-ray tube 12.

The X-ray detector 14 converts X-rays transmitted through a subject to electric charges and detect them. As an X-ray detector 14, a flat type X-ray detector (Flat Panel Detector) or those configured by combining an image intensifier and a TV camera may be used. The charges detected by the X-ray detector 14 are transmitted to the image processing device 1 as two-dimensional projection data. As described later, the two-dimensional projection data is converted into digital signals by the A/D (Analog/Digital) converter 26 and stored in a two-dimensional image memory 30.

The system control part (not illustrated) receives a command to acquire volume data. Based on this command, the X-ray imaging mechanism 10 acquires projection data (mask image) before the injection of a contrast agent. That is, via the mechanism control part, the system control part causes the arm 11 to rotate at a high speed like a propeller, e.g. 50 degrees/second before the contrast agent is injected into the blood vessel of the subject.

Accompanying this, the X-ray control part controls the high voltage generation part to control X-rays generated by the X-ray tube 12. The high voltage generation part generates a high voltage supplied to the X-ray tube 12. Furthermore, the system control part controls the irradiation field of X-rays by the X-ray diaphragm device via the mechanism control part. Thereby, the X-ray imaging mechanism 10 performs imaging, for example, at intervals of two degrees and acquires two-dimensional projection data of, for example, 100 frames by the X-ray detector 14.

Next, the mechanism control part of the X-ray imaging mechanism 10 drives the arm 11, returning the arm 11 to the start position of mask imaging. Thereafter, the system control part acquires the projection data of a contrast image after the contrast agent has been injected in the same way as the acquisition of the projection data of a mask image via the mechanism control part and the X-ray control part. After of a certain period of time has elapsed from the time when the contrast agent is injected into a subject by a contrast agent injector, the X-ray imaging mechanism 10 performs imaging, for example, at intervals of two degrees and acquires two-dimensional projection data of, for example, 100 frames by the X-ray detector 14.

The acquired two-dimensional projection data of the mask image and the contrast image are stored in the two-dimensional image memory 30 after having been converted into digital signals by the A/D converter 26 that is described later in the image processing device 1 in the same way as the two-dimensional projection data which is acquired prior to the injection of the contrast agent by the image processing device 1 to be described later.

(Configuration of Image Processing Device)

Figure 3:
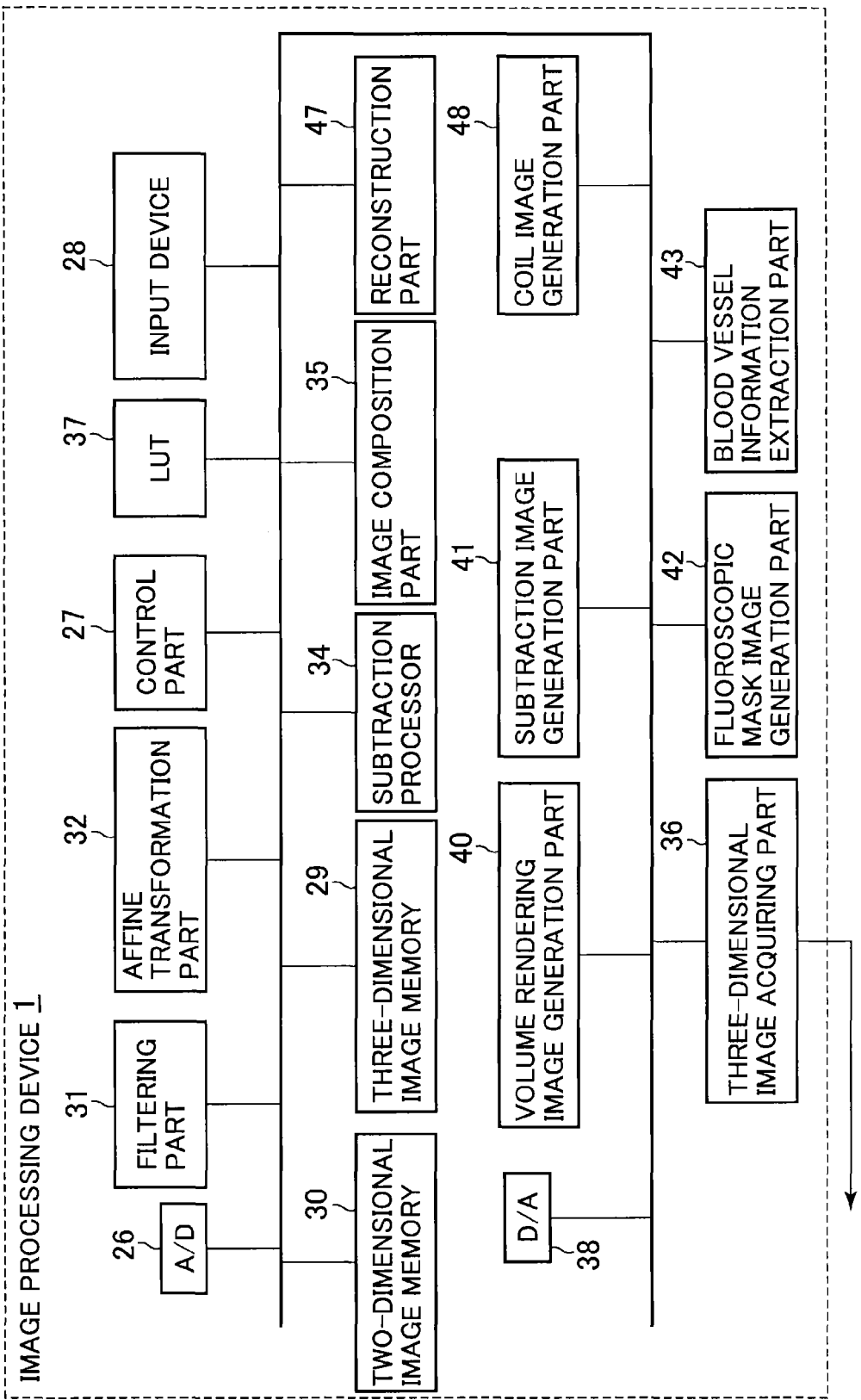
FIG. 3 is a schematic block diagram showing the functional configuration of an image processing device according to Embodiment 1.

Next, with reference to FIG. 1 and FIG. 3, the configuration of the image processing device 1 related to Embodiment 1 is described. FIG. 3 is a schematic block diagram showing the functional configuration of the image processing device 1 related to Embodiment 1. The image processing device 1 is connected to the X-ray detector 14 of the X-ray imaging mechanism 10 via the A/D converter 26.

As shown in FIG. 3, the image processing device 1 is configured comprising an A/D converter 26, a control part 27, a three-dimensional image memory 29, a two-dimensional image memory 30, a filtering part 31, an affine transformation part 32, a subtraction processor 34, an image composition part 35, a three-dimensional image acquiring part 36, an LUT (Look-up Table) 37, a volume rendering image generation part 40, a subtraction image generation part 41, a fluoroscopic mask image generation part 42, a blood vessel information extraction part 43, a reconstruction part 47, a coil image generation part 48, and a D/A converter (Digital/Analog) 38. A display 39 is connected to the image processing device 1 via the D/A convertor 38. Furthermore, an input device 28 comprising a road map switch is connected to the image processing device 1. The control part 27 controls each part of the image processing device 1.

<<Two-dimensional Image Memory, Filtering Part, and Affine Transformation Part>>

The two-dimensional image memory 30 stores two-dimensional projection data (X-ray image data) generated in the X-ray imaging mechanism 10 and converted into digital signals by the A/D converter 26. The projection data stored in the two-dimensional image memory 30 includes two-dimensional X-ray image data that has undergone filtering such as high frequency enhancement, etc. by the filtering part 31. Furthermore, the projection data to be stored therein includes projection data, etc. that has undergone an affine transformation such as image magnification, movement, etc. by the affine transformation part 32.

<<Subtraction Processor>>

The subtraction processor 34 performs subtraction processing on projected data of a mask image from the projection data of a contrast image stored in the two-dimensional image memory 30. To describe this processing, it is presumed that each mask image of the first to Nth frames and contrast image of the first to Nth frames have been imaged sequentially at the same angle.

For example, the subtraction processor 34 reads out, from the two-dimensional image memory 30, a mask image captured in the Nth frame and a contrast image captured in the Nth frame. Furthermore, the subtraction processor 34 converts these to natural logarithms. Thereafter, the subtraction processor 34 performs subtraction processing. As a result, the subtraction processor 34 ends up, from a mask image, performing subtraction processing on a contrast image with the same projection direction as the mask image. As described, the subtraction processor 34 performs subtraction processing on a contrast image from a mask image mutually having the same angle. It should be noted that subtraction processing is performed after both are converted to natural logarithms. Hereinafter, projection data subjected to subtraction processing is referred to as "DSA (Digital Subtraction Angiography) data."

The subtraction processor 34 transmits the DSA data of N frames (e.g. 100 frames) to the reconstruction part 47.

<<Reconstruction Part>>

The reconstruction part 47 receives DSA data of N frames from the subtraction processor 34. The reconstruction part 47 reconstructs volume data from this plurality of two-dimensional DSA data. As a reconstruction method, a filtered back projection method, etc. proposed by Feldkamp etc., is known. In case of filtered back projection, for example, the DSA data of 100 frames go through an appropriate convolution filter. As the convolution filter, for example, that by Shepp & Logan and Ramachandran is known.

The reconstruction part 47 obtains volume data (reconstruction data) by back-projection calculation. Herein, a reconstruction region is defined as a cylinder that is in inner contact with a flux of X-rays in all directions of an X-ray tube. The inside of the cylinder, for example, is three-dimensionally discretized by a length d in the center part of the reconstruction region projected to the width of one detection element of the X-ray detector 14, and is required to obtain a reconstructed image of the data of the discrete points. It should be noted that herein one example of the discretization interval is shown, but a discretization interval defined according to a device may be used.

The reconstruction part 47 stores volume data in the three-dimensional image memory 29. It should be noted that in the above, volume data is generated by reconstructing DSA data that has been subjected to subtraction processing. However, without being limited to this configuration, a configuration such as the one next is also possible. For example, the image processing device 1 generates volume data that has been reconstructed from the projection data of mask images by the reconstruction part 47. Furthermore, the image processing device 1 generates volume data that has been reconstructed from contrast images by the reconstruction part 47. The subtraction processor 34 may also perform subtraction processing on the volume data of mask images and the volume data of contrast images.

<<Three-Dimensional Image Memory>>

The three-dimensional image memory 29 stores the volume data received from the reconstruction part 47.

Furthermore, instead of the volume data received from the reconstruction part 47, volume data received from an external device may also be stored in the three-dimensional image memory 29. The external device is, for example, a medical diagnostic device such as an X-ray CT device, MRI device, etc. or PACS, etc. CTA (Computed Tomography Angiography) is obtained from the X-ray CT device. MRA (Magnetic Resonance Angiography), non-contrast MRA (Magnetic Resonance Angiography), etc. are obtained from the MRI device. Moreover, in case of obtaining volume data from an external device, a three-dimensional image acquiring part 36 acquires volume data from outside, for example, via a network.

Furthermore, in case of including human body information in addition to blood vessel information in the volume data from outside, the blood vessel information is extracted by employing a method such as threshold processing, range designation of pixel values or region growing, etc. by a blood vessel information-extraction part 43, and the volume data is generated. Otherwise, the blood vessel information may also be extracted to generate volume data by combining methods threshold processing, range designation of pixel values, regional growth, etc.

<<Fluoroscopic Mask Image Generation Part>>

The fluoroscopic mask image generation part 42 receives a command to generate a fluoroscopic mask image M from the control part 27. For example, this command is given when an operator conducts an operation to command the start of fluoroscopic imaging via the input device 28. That is, when receiving the command to start fluoroscopic imaging, the X-ray imaging apparatus performs imaging the subject by the X-ray imaging mechanism 10. The projection data of several frames is acquired from the imaging. The projection data is converted to digital signals and transmitted to the image processing device 1. The control part 27 of the image processing device 1 gives a command to the fluoroscopic mask image generation part 42 to generate a fluoroscopic mask image M.

The fluoroscopic mask image generation part 42 obtains projection data of several frames acquired by the fluoroscopic imaging and generates a fluoroscopic mask image M averaged for, for example, one second before being stored in the two-dimensional image memory 30.

It should be noted that upon generation of the fluoroscopic mask image M, a dynamic image generation part (not illustrated) generates a real time fluoroscopic image R. That is, a subject is subjected to imaging by the X-ray imaging apparatus using the X-ray imaging mechanism 10 at a predetermined interval. The projection data is sequentially acquired from this imaging. The sequentially acquired projection data is transmitted to the image-processing device 1. The image-processing device 1 receives the projection data and converts the projection data into digital signals. Furthermore, the control part 27 of the image processing device 1 gives a command to generate a real time fluoroscopic image R to the dynamic image generation part. The dynamic image generation part acquires the projection data that has been sequentially acquired by the fluoroscopic imaging, sequentially generates real time fluoroscopic images R, and stores the real time fluoroscopic images R in the two-dimensional image memory 30. When moved into a real time fluoroscopic image acquisition phase, due to the command from the X-ray imaging apparatus, device operations such as with a catheter, guide wire, etc. begin.

<<Subtraction Image Generation Part>>

When the fluoroscopic mask image M and the real time fluoroscopic image R are stored in the two-dimensional image memory 30, the control part 27 causes the subtraction image generation part 41 to generate fluoroscopic subtraction data. That is, the control part 27 reads out, from the two-dimensional image memory 30, image data or projection data of fluoroscopic mask images M and real time fluoroscopic images R that have been continuously acquired. The control part 27 transmits the data to the subtraction image generation part 41. The subtraction image generation part 41 performs subtraction processing on the real time fluoroscopic image R from the fluoroscopic mask image M to generate a fluoroscopic subtraction image by fluoroscopic imaging. It should be noted that if devices such as a guide wire, catheter, etc. have been inserted into the subject and also if the devices have moved from the time when the fluoroscopic mask image M was acquired, the fluoroscopic subtraction image includes data showing the devices.

Furthermore, for a fluoroscopic subtraction image, it is preferable to perform an enhancing process for devices such as a catheter, guide wire, etc. that have been inserted into the subject. By performing the enhancing process for devices in the fluoroscopic subtraction image, a device-enhanced image D (ref. FIG. 2) is generated. For example, as an enhancing process for devices, a noise reduction process is performed. As such a noise reduction process, it is possible to adopt a median filtering process.

Furthermore, as a further enhancing process for devices, it is also possible to perform a detection process of a line component to a fluoroscopic subtraction image or a device-enhanced image D. By performing the detection process on a line component, noise components are reduced in an image without deteriorating the line component. As a result, device portions such as a guide wire, catheter, etc. can be relatively enhanced in the image.

In FIG. 2, a symbol "−" displayed between a real time fluoroscopic image and a fluoroscopic mask image means subtraction processing. Furthermore, FIG. 2 shows the steps for creating a device-enhanced image D by performing a noise-suppression process and a wire-enhancing process on a fluoroscopic subtraction image. As a guide wire-enhancing process, for example, a process exists for enhancing a high frequency component in a fluoroscopic subtraction image.

It should be noted that in some cases, these fluoroscopic subtraction images or device-enhanced images D are transmitted to the display 39 after having been composed with other images (volume rendering image V, etc.). Furthermore, sometimes a fluoroscopic subtraction image or a device-enhanced image D is transmitted to the display without being composed with other images.

<<Volume Rendering Image Generation Part>>

The volume rendering image generation part 40 reads out volume data from the three-dimensional image memory 29 and generates a volume rendering image V. That is, when an operator presses the 3D road map switch, the control part 27 of the image processing device 1 commands the volume rendering image generation part 40 to generate a volume rendering image V.

When the command to generate a volume rendering image V is received from the control part 27, the volume rendering image generation part 40 executes a process such as volume rendering, etc. to generate a volume rendering image (three-dimensional blood vessel display image). A process such as volume rendering is performed in accordance with information indicating the state of the X-ray imaging apparatus (medical image diagnosis apparatus). That is, the volume rendering image generation part 40 performs the above process so as to match the state of an X-ray imaging apparatus, for example, a state indicated by information such as the observation angle, observation field of vision, observation magnification rate, observation position, etc.

<<Coil Image Generation Part>>

The coil image generation part 48 performs a coil extraction process on a fluoroscopic mask image M. Due to the coil extraction process, in the fluoroscopic mask image M, a portion showing a coil that has been placed in a subject is extracted to generate a coil-extracted image C. As such a coil extraction process, a low pass filter process with respect to the fluoroscopic mask image M may be adopted. Due to the low pass filter process of the coil image generation part 48, an image from which a low frequency component is removed from a fluoroscopic mask image M is obtained. The coil image generation part 48 transmits this image to the subtraction processor 34 and causes the subtraction processor 34 to perform a subtraction process on the image and the fluoroscopic mask image.

The coil image generation part 48 receives image data subjected to the subtraction process by the subtraction processor 34 or image data subjected to a device-enhancing process, etc. Furthermore, the image data is subjected to threshold value processing by the coil image generation part 48. That is, the coil image generation part 48 performs a process to divide an image into a portion showing a coil and other portions, based on the pixel value in the image data.

The X-ray absorption rate of a coil is evidently higher in comparison to other sites and, hence, different from pixel values of other sites. Therefore, the coil image generation part 48 performs subtraction processing on an original fluoroscopic mask image M from an image that has been subjected to the low pass filter process, thus, making it possible to compress the background. Moreover, extracting a portion showing a coil by a threshold value corresponding to the pixel value becomes possible as the image data after having been subjected to subtraction processing is subjected to the threshold value process by the coil image generation part 48. As described, the coil image generation part 48 generates a coil-extracted image C.

<<Image Composition Part>>

As shown in FIG. 2, the image composition part 35 cumulatively composes arbitrary combinations of a fluoroscopic subtraction image or a device-enhanced image D, a volume rendering image V, a real time fluoroscopic image R, and a coil-extracted image C. It should be noted that the symbol "+" displayed in FIG. 2 means composition processing.

Furthermore, the image composition part 35 is capable of changing the composition ratio of each image via a composition ratio-changing part (not illustrated). That is, when an operation to change the composition ratio of each image is carried out by the input device 28, the composition ratio-changing part changes the transparency degree of each image (layer) according to the operation. For example, in order to grasp the movement of a guide wire, etc., when fluoroscopic imaging starts, the transparency degree of the layer of a device-enhanced image D (guide wire image, etc.) extracted in a 3D road map image S is lowered such that it is close to non-transparent. Under this condition, when the image composition part 35 composes images, the readability of devices is improved as device portions such as a guide wire, etc. are enhanced in an image. Likewise, the composition ratio-changing part is capable of relatively enhancing device portions by making the layer of other portions (real time fluoroscopic image R, etc.) in the 3D road map image S close to transparent.

In other words, the image composition part 35 composes and displays each image based on an initial value (default value) of the composition ratio of each image and, after the change in the composition ratio is made by the composition ratio-changing part, it is possible to compose each image based on the composition ratio after the change. For example, in order to grasp the movement of a subject from the volume data acquisition time until fluoroscopy starts, the ratio of the layer of a real time fluoroscopic image is increased for the display at the time when fluoroscopy starts (default value).

Further, after having been confirmed that there is no movement of the subject, it is also possible to improve the readability of a device image such as guide wire, etc. or of a volume rendering image by lowering the ratio of the layer of a real time fluoroscopic image by the composition ratio-changing part.

Through this processing, the image composition part 35 generates a 3D road map image S. Furthermore, it is also possible to compose a coil-extracted image C so as to be displayed with a color that is different from the background, the device-enhanced image D, the real time fluoroscopic image R, and the volume rendering image V. Using a LUT 37, the image composition part 35 is capable of assigning a unique color to the road map portion of the composite image and changing the tonal gradation.

It should be noted that when an operator conducts intervention treatment, etc. following a command to start fluoroscopic imaging, insertion of devices, pressing the road map switch, and placing a coil sequentially in this order, the image composition part 35 behaves as below.

When the image processing device 1 receives a command to start fluoroscopic imaging via an input device 28, the image composition part 35 receives a fluoroscopic subtraction image or a device-enhanced image D, and a real time fluoroscopic image R. The image composition part 35 composes these to cause the display 39 to display.

When an operator inserts a guide wire and a catheter into a subject and gives a command to enhance these devices via the input device 28, the image composition part 35 receives a device-enhanced image D and a real time fluoroscopic image R. The composition ratio-changing part adjusts the transparency degree of these images as described above. The image composition part 35 composes these to cause the display 39 to display.

When an operator presses the road map switch, the image composition part 35 receives a device-enhanced image D, a real time fluoroscopic image R, and a volume rendering image V. The image composition part 35 composes these to cause the display 39 to display.

When the operator places a coil into an aneurysm, etc. of the subject and gives a command for reimaging as well as a command for coil extraction via the input device 28, the image composition part 35 receives a device-enhanced image D, a real time fluoroscopic image R, a volume rendering image V, and a coil-extracted image C. The composition ratio-changing part adjusts the transparency degree of these images as described above. The image composition part 35 composes these to cause the display 39 to display.

(Operation of Image Processing Device)

Next, details of the processing of the aforementioned, with reference to FIG. 2, image processing device 1 are described with reference to the flow charts of FIG. 4 to FIG. 6.

<<Generation of Volume Data>>

Figure 4:
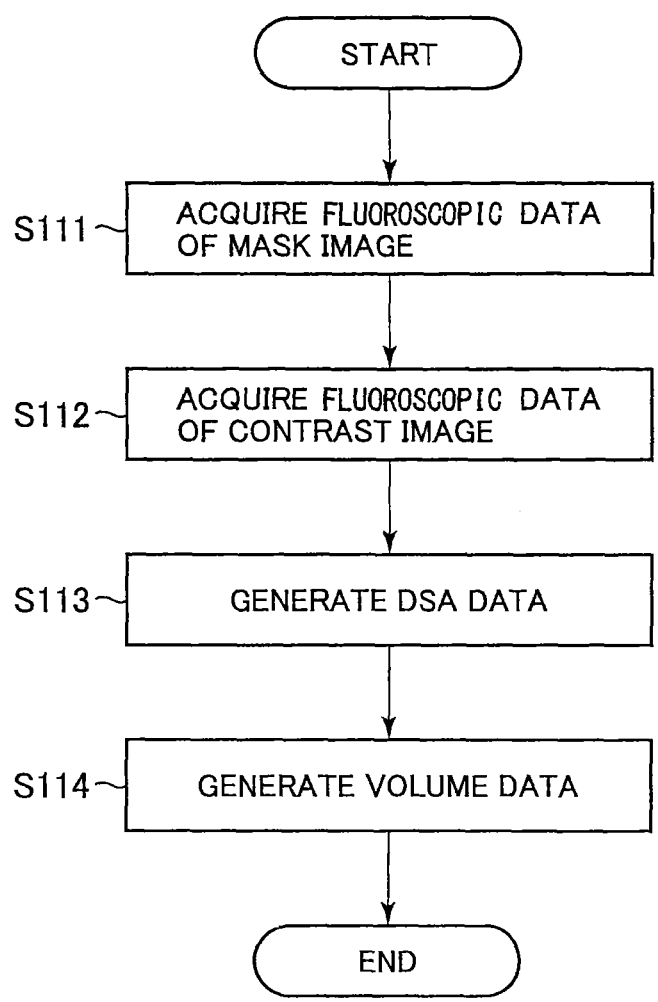
FIG. 4 is a schematic flow chart showing the steps of a process to generate volume data by the X-ray imaging apparatus of Embodiment 1.

With reference to FIG. 4, the steps for generating volume data by an X-ray imaging apparatus in the present embodiment are described. FIG. 4 is a schematic flow chart showing the steps of a process to generate volume data by the X-ray imaging apparatus in Embodiment 1.

(S111)

According to the operation of the input device 28 by an operator, the X-ray imaging mechanism 10 receives a command to acquire volume data. Based on this command, via the mechanism control part, before injecting a contrast agent, the system control part of the X-ray imaging mechanism 10 causes the arm 11 to rotate at a high speed like a propeller, for example, at 50 degrees/sec, and performs X-ray imaging on the subject. Thereby, the X-ray imaging apparatus acquires projection data of a mask image captured before the contrast agent is injected. The projection data is transmitted to the image processing device 1. The image processing device 1 converts the projection data into digital signals by the A/D converter 26, and stores the digital signals in the two-dimensional image memory 30.

(S112)

Once the projection data of the mask image is acquired, the contrast agent is injected into the subject. After injection of the contrast agent, the system control part of the X-ray imaging mechanism 10 performs X-ray imaging on the subject in the same way as mask images via the mechanism control part. Thereby, the X-ray imaging apparatus acquires projection data of contrast images. The projection data is transmitted to the image processing device 1. The image processing device 1 converts the projection data to digital signals by the A/D converter 26 and stores the projection data in the two-dimensional image memory 30.

(S113)

The subtraction processor 34 reads out a mask image captured in the Nth frame and a contrast image captured in the Nth frame from the two-dimensional image memory 30. Furthermore, the subtraction processor 34 converts these to natural logarithms. Thereafter, the subtraction processor 34 performs subtraction processing on these images at the same angle. DSA data is generated by this process. The subtraction processor 34 repeats this process for a predetermined number of frames. After the process for the predetermined number of frames is complete, the subtraction processor 34 transmits the DSA data to the reconstruction part 47.

(S114)

The reconstruction part 47 receives the DSA data. The reconstruction part 47 reconstructs volume data from the DSA data. The reconstruction part 47 generates volume data that has been reconstructed by the process. The volume data is stored in the three-dimensional image memory 29.

<<Fluoroscopic Imaging>>

After acquiring the volume data in the X-ray imaging apparatus, a shift to a treatment phase subsequently takes place. First, the generation steps of a device-enhanced image D showing a device that is inserted into a subject are described with reference to FIG. 5. FIG. 5 is a schematic flow chart showing the steps for a generation process of a device-enhanced image D by the X-ray imaging apparatus in Embodiment 1.

(S201)

To insert a guide wire, catheter, etc. close to the aneurysm in the subject, a doctor etc. presses a fluoroscopic imaging switch (not illustrated) in the input device 28. The X-ray imaging mechanism 10 determines whether or not the fluoroscopic imaging switch has been pressed.

(S202)

When it is determined that the fluoroscopic imaging switch has been pressed (S201; Yes), the X-ray imaging mechanism 10 performs several frames of imaging on the subject. The image processing device 1 receives projection data of several frames detected by the X-ray detector 14 and, after converting the projection data into digital signals, transmits the digital signals to the fluoroscopic mask image generation part 42. The fluoroscopic mask image generation part 42 averages the projection data of the mask images to generate a fluoroscopic mask image M and stores the fluoroscopic mask image M in the two-dimensional image memory 30.

(S203)

The X-ray imaging mechanism 10 performs imaging at a predetermined interval. Projection data sequentially acquired from the imaging is converted into digital signals by the image processing device 1 and transmitted to a dynamic image generation part (not illustrated). The dynamic image generation part acquires the projection data that has been sequentially acquired by fluoroscopic imaging, sequentially generates real time fluoroscopic images R, and stores the real time fluoroscopic images R in the two-dimensional image memory (S204)

The control part 27 reads out, from the two-dimensional image memory 30, the image data or the projection data of a fluoroscopic image M and a real time fluoroscopic image R that have been continuously being acquired, and transmits the image data or the projection data to the subtraction image generation part 41. The subtraction image generation part 41 performs a subtraction process on the real time fluoroscopic image R from the fluoroscopic mask image M to generate a fluoroscopic subtraction image by fluoroscopic imaging.

(S205)

Furthermore, when necessary, the subtraction image generation part 41 performs an enhancing process of devices on the fluoroscopic subtraction image. For example, as a process for enhancing a device, a noise reduction process such as a median filtering process, etc., is performed. Moreover, the subtraction image generation part 41 performs a noise reduction process such as a detection process of a line component. As a result of a noise suppression process on the fluoroscopic subtraction image by the subtraction image generation part 41, a noise-suppressed image (not illustrated) is generated.

(S206)

The subtraction image generation part 41 performs a wire-enhancing process such as a process to enhance a high frequency component in a noise-suppressed image, generating a device-enhanced image D. It should be noted that until a command to generate a 3D road map image S is given, sometimes the device-enhanced image D is transmitted to the display 39 without being composed with a volume rendering image V.

<<Composition of Images (Generation of 3D Roadmap Images)>>

Next, the generation step of a 3D road map image S in a treatment phase is described with reference to FIG. 6. FIG. 6 is a schematic flow chart showing the steps for the generation process of the 3D road map image S by the X-ray imaging apparatus in Embodiment 1.

(S207)

Before and after a fluoroscopic imaging switch is pressed to display a fluoroscopic subtraction image or a device-enhanced image D, a doctor inserts a guide wire, catheter, etc. in the vicinity of the aneurysm while referencing the image that is being displayed. Once the device is inserted in the vicinity of the aneurysm, the operator presses the 3D road map switch in the input device 28 for the purpose of accurately grasping the position of the aneurysm and verifying the inserted state of a coil into the aneurysm. The image processing device 1 determines whether or not the 3D road map switch has been pressed.

(S208)

When it is determined that the 3D road map switch has been pressed (S207; Yes), the image processing device 1 causes the volume rendering image generation part 40 to generate a volume rendering image V. That is, the volume rendering image generation part 40 reads out volume data from the three-dimensional image memory 29. The volume rendering image generation part 40 executes a process such as volume rendering, etc. on the volume data to generate a volume rendering image V. The process of the volume rendering, etc. is performed so as to be matched with a state indicated by information such as the observation angle, observation field of vision, observation magnification rate, observation position, etc. in the X-ray imaging apparatus.

(S209)

The image processing device 1 determines, after step 206, whether or not the imaging conditions in the X-ray imaging apparatus (X-ray imaging mechanism 10) have changed. Changes in the imaging conditions include the observation angle, magnification rate, bed movement, patient movements, etc. The information is based on information from the X-ray imaging mechanism 10, or determined by the control part 27 etc. based on fluoroscopic images. It should be noted that the determination for changes of the above conditions is described after the step 207 or the step 208 for convenience of description in FIG. 6, the timing of determination is not limited to the pattern of FIG. 6. Moreover, there are also cases in which changes of imaging conditions are designated via the input device 28.

(S210)

If the image processing device 1 determines that there have been changes in the imaging conditions (S209; Yes), imaging of the subject is performed for several frames by the X-ray imaging mechanism 10. After receiving the projection data of several frames detected by the X-ray detector 14 and converting the projection data into digital signals, the image processing device 1 transmits the digital signals to the fluoroscopic mask image generation part 42. The fluoroscopic mask image generation part 42 averages the projection data of mask images to generate a fluoroscopic mask image M and stores the fluoroscopic mask image M in the two-dimensional image memory 30.

(S211)

The coil image generation part 48 reads out a fluoroscopic mask image M from the two-dimensional image memory 30. The coil image generation part 48 performs coil extraction processing on the read out fluoroscopic mask image M. For example, with respect to the fluoroscopic mask image M, the coil image generation part 48 removes low frequency components by a low pass filtering process. Furthermore, the image and the fluoroscopic mask image M are subjected to subtraction processing. Moreover, by performing a threshold process, the coil image generation part 48 extracts a portion at which a coil is shown by a threshold value corresponding to the pixel value of the coil. Whereby, the coil image generation part 48 generates a coil-extracted image C.

(S212)

Until the 3D road map switch is pressed (S207; No), the image composition part 35 cumulatively composes a device-enhanced image D (subtraction image) and a real time fluoroscopic image R.

Until changes of the imaging conditions are made (S209; No), the image composition part 35 cumulatively composes a device-enhanced image D (subtraction image), a real time fluoroscopic image R, and a volume rendering image V. Thereby, a 3D road map image S is generated.

Once the coil-extracted image C is generated, the image composition part 35 cumulatively composes a device-enhanced image D (subtraction image), a real time fluoroscopic image R, a volume rendering image V, and a coil-extracted image C. Thereby, a 3D road map image S is generated.

It should be noted that the image composition part 35 is capable of composing each image and displaying the each image in a different color. Furthermore, the composition ratio of each image may be changed by the composition ratio-changing part. Due to the changes in the composition ratio of each image, the transparency degree of each image (layer) may be made different. The transparency degree of each image may be appropriately changed. That is, when a fluoroscopy starts (default value), in order to grasp the movement of the subject, the ratio of the layer of a real time fluoroscopic image R is increased to display. Further, after having been confirmed that there is no movement of the subject, it is also possible to improve the readability of a device image such as a guide wire, etc. or a volume rendering image by lowering the ratio of the layer of the real time fluoroscopic image R by the composition ratio-changing part.

The composed image data is converted into analogue by the D/A converter 38 and transmitted to the display 39. It should be noted that the analogue conversion process may sometimes be omitted depending on the display 39. Based on the analogue or digital image data received from the image processing device 1, the display 39 displays a 3D road map image S and a device-enhanced image D, etc.

As described above, Embodiment 1 is useful for devices to be used for supporting medical actions and particularly, suitable for cases in which a device operator such as a doctor visually recognizes a guide wire, catheter, coil, etc. and efficiently conducts medical actions.

[Embodiment 2]

Next, an X-ray imaging apparatus related to Embodiment 2 is described.

(Outline of the Operation)

First, with reference to FIG. 1, the outline of the operation of an image processing device 1 and an X-ray imaging mechanism 10 related to Embodiment 2 is described. The X-ray imaging mechanism 10 shown in FIG. 1 acquires volume data (three-dimensional vascular image data), as one example, as described below. The volume data is data for generating a volume rendering image V.

The X-ray imaging apparatus related to Embodiment 2 acquires a plurality of frames of projection data of two-dimensional mask images while causing the X-ray imaging mechanism 10 to rotate around a subject at a high speed. Next, the plurality of frames of projection data of the two-dimensional contrast images are acquired while rotating the X-ray imaging mechanism 10 again around the subject into which a contrast agent has been injected.

A mask image acquired at a certain angle and a contrast image acquired at the same angle are subjected to subtraction processing. DSA (Digital Subtraction Angiography) data is obtained by this subtraction processing.

Next, the DSA data is reconstructed to obtain volume data in which a vascular image is enhanced. The reconstructed volume data is stored in a three-dimensional image memory.

Next, the X-ray imaging apparatus generates a volume rendering image V, for example, as described below. Furthermore, a composite image of the volume rendering image V and a fluoroscopic subtraction image is generated.

The X-ray imaging apparatus starts fluoroscopic imaging based on an operation by a user. After starting fluoroscopic imaging, the X-ray imaging apparatus acquires fluoroscopic mask image data. Furthermore, the X-ray imaging apparatus acquires real time fluoroscopic image data. Moreover, the X-ray imaging apparatus generates fluoroscopic subtraction data by subtraction processing. Along with these processes, (1) the X-ray imaging apparatus enhances and displays a guide wire, catheter, etc. in the subject. Furthermore, (2) it is determined whether or not a command is received to generate a 3D road map. Moreover, (3) it is determined whether or not there are condition changes in imaging. (4) The composition ratio of a real time fluoroscopic image R is automatically reduced as the time elapses after fluoroscopy starts. Hereinafter, the outline of processes (1) to (4) is described.

(1) After starting the fluoroscopic imaging, a device such as a guide wire, catheter, etc. is inserted into the subject by a doctor while using fluoroscopic images as references. Then, the image processing device 1 performs detection processing, etc. on a line component with respect to the fluoroscopic subtraction data. As a result, other portions except those showing devices such as the guide wire, catheter, etc. in the fluoroscopic subtraction data, that is, noise, are suppressed. Consequently, in the fluoroscopic subtraction data, portions showing devices are displayed as relatively enhanced in comparison to the other portions.

(2) The X-ray imaging apparatus determines whether or not a command has been received to generate a 3D road map, for example, after inserting a device into the subject. The command is based on an operation by a doctor etc. If a command for generation is received, the X-ray imaging apparatus obtains volume data from the three-dimensional image memory. Furthermore, the X-ray imaging apparatus generates a volume rendering image V by performing a process such as volume rendering, etc. on the volume data. The process of volume rendering, etc. is, for example, executed according to the state indicated by information regarding the angle, field of vision, magnification rate, position, etc. of observation.

Furthermore, the X-ray imaging apparatus generates and displays a 3D road map image based on the fluoroscopic subtraction data of the above (1) and the volume rendering image, etc. of (2).

(3) The X-ray imaging apparatus determines whether or not there are any changes in conditions for imaging due to the observation angle, the magnification rate, the shifts of the bed, movement of the patient, etc. Furthermore, it is determined whether or not a command has been received to regenerate a fluoroscopic mask image M. If determined that there were the changes in the conditions or the command has been given, the X-ray imaging apparatus obtains volume data and regenerates the volume rendering image V in accordance with the condition changes. Moreover, the X-ray imaging apparatus generates a fluoroscopic mask image M and a real time fluoroscopic image R according to the condition changes.

(4) The composition ratio of a real time fluoroscopic image is automatically reduced by the X-ray imaging apparatus as the time elapses after fluoroscopy starts. Thereby, a three-dimensional vascular image and a device-enhanced image D are enhanced; hence, making it easy to visually recognize a guide wire, etc.

Figure 7:
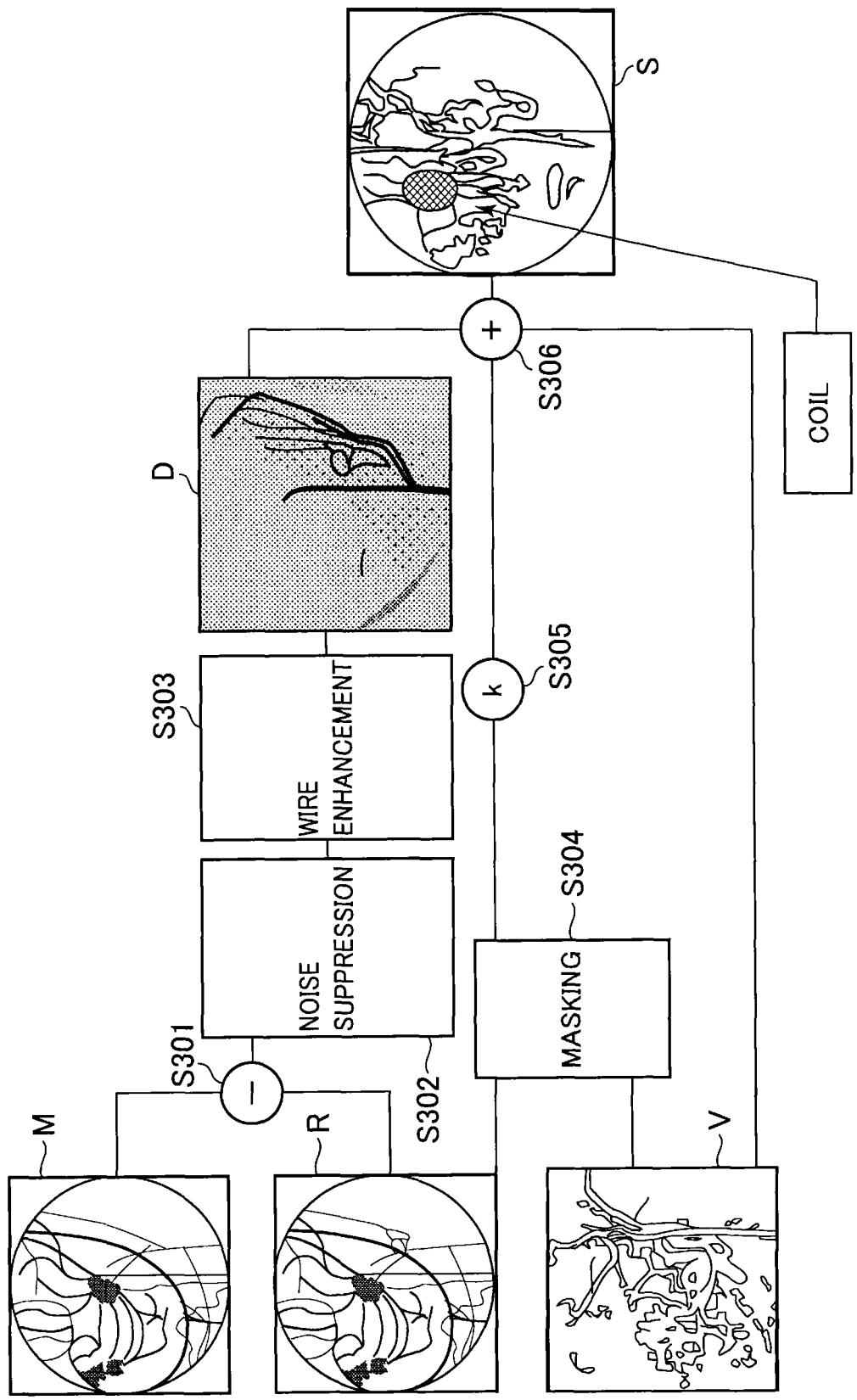
FIG. 7 is a schematic block diagram schematically showing the steps to generate a 3D road map image by the X-ray imaging apparatus of Embodiment 2.

Next, with reference to FIG. 7, the operation outline of the image processing device 1 in accordance with the condition changes in imaging or the command to regenerate a fluoroscopic mask image M is described. It should be noted that the operation is an example of coil embolization with respect to aneurysms. FIG. 7 is a schematic block diagram schematically showing the steps to generate a 3D road map image S by the X-ray imaging apparatus of Embodiment 2.

<<Generation of Device-Enhanced Images>>

The image processing device 1 obtains fluoroscopic subtraction data by subtraction processing on the fluoroscopic mask image M and the real time fluoroscopic image R (S301). In FIG. 7, a symbol "−" displayed between the real time fluoroscopic image R and the fluoroscopic mask image M means subtraction processing. Furthermore, the image processing device 1 performs noise suppression processing on the fluoroscopic subtraction data (S302).

The image processing device 1 performs detection processing of a line component, etc. (enhancement of a wire) on the fluoroscopic subtraction data subjected to noise suppression processing. As a result, a device-enhanced image D in which a device such as a guide wire, etc. is relatively enhanced in the fluoroscopic image, is generated (S303).

<<Masking Processing and Adjustment of Composition Ratio>>

The image processing device 1 performs masking processing on the real time fluoroscopic image R. For example, the image processing device 1 performs a process to lower the composition ratio of the real time fluoroscopic image R only with respect to a superposed portion of the real time fluoroscopic image R and a portion at which a blood vessel in the volume rendering image V is present. Due to this process, even if the composition ratio of the real time fluoroscopic image R is increased, it is possible to avoid deterioration of the readability of the volume rendering image V (S304). Furthermore, the image processing device 1 chronologically reduces the composition ratio of the real time fluoroscopic image R by multiplying by a readability coefficient k with respect to the real time fluoroscopic image R such that a device in a composite image is relatively enhanced (S305).

<<3D Roadmap Image>>

Composition processing of the device-enhanced image D, and the real time fluoroscopic image R subjected to masking processing is performed by the image processing device 1 (Step S306). Furthermore, the volume rendering image V and the image data subjected to the composition processing are further subjected to composition processing to generate a 3D road map image S. Moreover, the image processing device 1 causes the display 39 to display the 3D road map image S.

As described, the X-ray imaging apparatus related to Embodiment 2 composes and displays a real time fluoroscopic image R, a volume rendering image V, and a device-enhanced image D, etc. Thereby, it becomes possible for the user to grasp the positional relationship of blood vessels and the structure inside the subject. Consequently, it is possible for the user to grasp the relative positional changes of the subject and an imaging mechanism in the event of displacement. Furthermore, the image processing device 1 chronologically reduces the composition ratio of the real time fluoroscopic image R. by multiplying by the readability coefficient k with respect to the real time fluoroscopic image R; thereby, a device in a composite image is relatively enhanced (Entire Configuration of X-ray Imaging Apparatus)

Next, with reference to FIG. 1, the configuration of the X-ray imaging apparatus related to Embodiment 2 is described. As shown in FIG. 1, the X-ray imaging apparatus related to Embodiment 2 is configured including an X-ray imaging mechanism 10, an image processing device 1, and a display 39. Furthermore, the X-ray imaging apparatus comprises a system control part (not illustrated).

The system control part that is not illustrated controls the entire X-ray imaging apparatus such as the image processing device 1 and the X-ray imaging mechanism 10, etc.

An input device 28 includes, for example, a keyboard, a mouse and further, a road map switch. The road map switch is for inputting a command to compose a road map of blood vessels (3D road map image S) with respect to a current fluoroscopic image.

The display 39 receives each image data from the image processing device 1 and displays a fluoroscopic image, a device-enhanced image D, a 3D road map image S, etc.

It should be noted that the specific content of the X-ray imaging apparatus is the same as Embodiment 1; hence, a description is omitted.

(Configuration of Image Processing Device)

Figure 8:
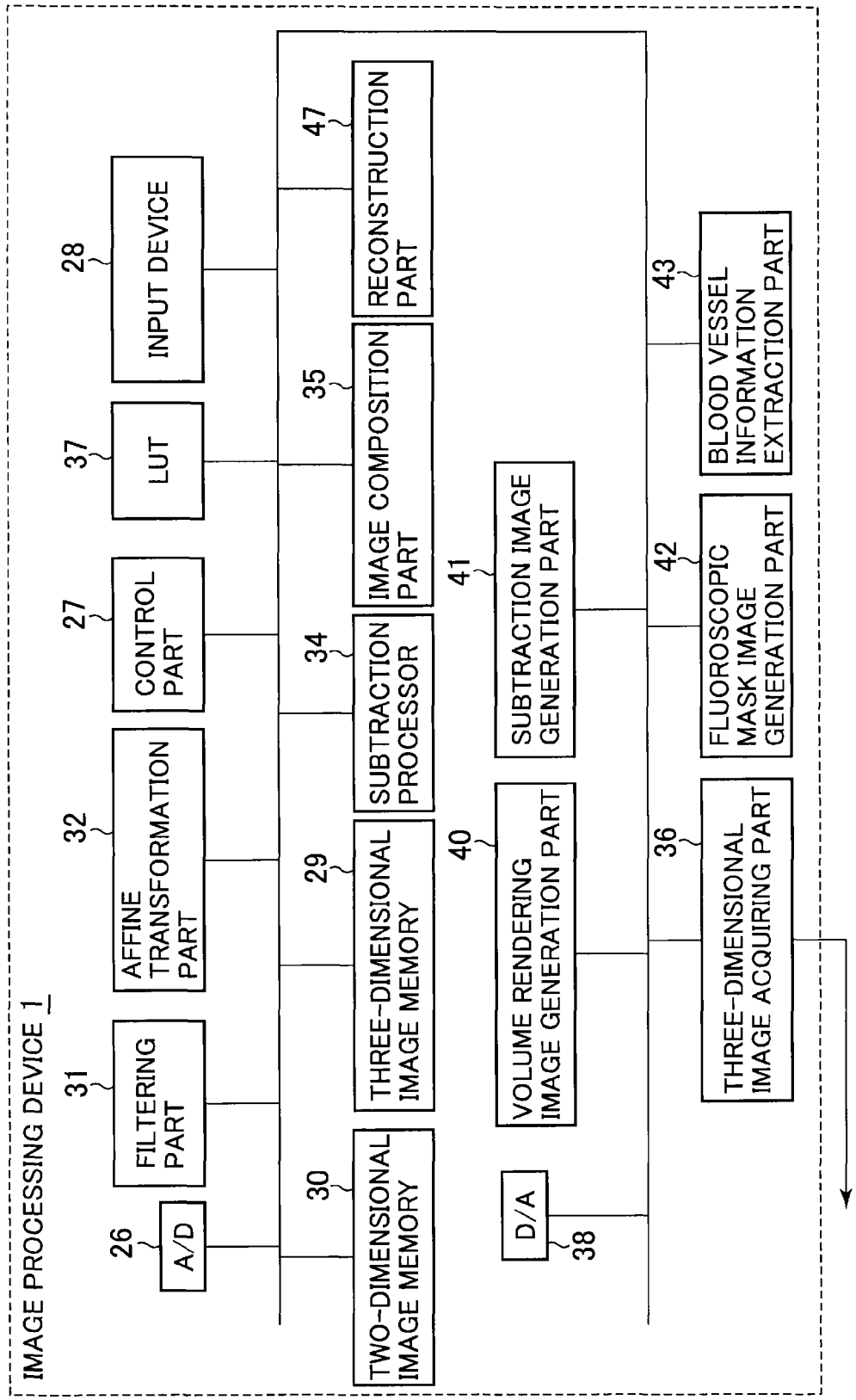
FIG. 8 is a schematic block diagram showing the functional configuration of an image processing device according to Embodiment 2.

Next, with reference to FIG. 1 and FIG. 8, the configuration of the image processing device related to Embodiment 2 is described. FIG. 8 is a schematic block diagram showing a functional configuration of the image processing device 1 related to Embodiment 2. The image processing device 1 is connected to the X-ray detector 14 of the X-ray imaging mechanism 10 via the A/D converter 26.

As shown in FIG. 8, the image processing device 1 is configured comprising an A/D converter 26, a control part 27, a three-dimensional image memory 29, a two-dimensional image memory 30, a filtering part 31, an affine transformation part 32, a subtraction processor 34, an image composition part 35, a three-dimensional image acquiring part 36, an LUT (Look-up Table) 37, a volume rendering image generation part 40, a subtraction image generation part 41, a fluoroscopic mask image generation part 42, a blood vessel information extraction part 43, a reconstruction part 47, and a D/A converter (Digital/Analog) 38. A display 39 is connected to the image processing device 1 via the D/A convertor 38. Furthermore, an input device 28 comprising a road map switch is connected to the image processing device 1. The control part 27 controls each part of the image processing device 1. It should be noted that the coil image generation part 48 is not included in Embodiment 2.

<<Two-Dimensional Image Memory, Filtering Part, and Affine Transformation Part>>

The two-dimensional image memory 30 stores two-dimensional projection data (X-ray image data) generated in the X-ray imaging mechanism 10 and converted into digital signals by the A/D converter 26. The projection data stored in the two-dimensional image memory 30 includes two-dimensional X-ray image data that has undergone filtering such as high frequency enhancement, etc. by the filtering part 31. Furthermore, the projection data to be stored therein includes projection data, etc. that has undergone an affine transformation such as image magnification, movement, etc. by the affine transformation part 32.

<<Subtraction Processor>>

The subtraction processor 34 performs subtraction processing on projected data of a mask image from the projection data of a contrast image stored in the two-dimensional image memory 30. To describe this processing, it is presumed that each mask image of the first to Nth frames and contrast image of the first to Nth frames have been imaged sequentially at the same angle.

For example, the subtraction processor 34 reads out, from the two-dimensional image memory 30, a mask image captured in the Nth frame and a contrast image captured in the Nth frame. Furthermore, the subtraction processor 34 converts these to natural logarithms. Thereafter, the subtraction processor 34 performs subtraction processing. As a result, the subtraction processor 34 ends up, from a mask image, performing subtraction processing on a contrast image with the same projection direction as the mask image. As described, the subtraction processor 34 performs subtraction processing on a contrast image from a mask image mutually having the same angle. It should be noted that subtraction processing is performed after both are converted to natural logarithms. Hereinafter, projection data subjected to subtraction processing is referred to as "DSA (Digital Subtraction Angiography) data."

The subtraction processor 34 transmits the DSA data of N frames (e.g. 100 frames) to the reconstruction part 47.

<<Reconstruction Part>>

The reconstruction part 47 receives DSA data of N frames from the subtraction processor 34. The reconstruction part 47 reconstructs volume data from this plurality of two-dimensional DSA data. As a reconstruction method, a filtered back projection method, etc. proposed by Feldkamp etc., is known.

In case of filtered back projection, for example, the DSA data of 100 frames go through an appropriate convolution filter. As the convolution filter, for example, that by Shepp & Logan and Ramachandran is known.

The reconstruction part 47 obtains volume data (reconstruction data) by back projection calculation. Herein, a reconstruction region is defined as a cylinder that is in inner contact with a flux of X-rays in all directions of an X-ray tube. The inside of the cylinder, for example, is three-dimensionally discretized by a length d in the center part of the reconstruction region projected to the width of one detection element of the X-ray detector 14, and is required to obtain a reconstructed image of the data of the discrete points. It should be noted that herein one example of the discretization interval is shown, but a discretization interval defined according to a device may be used.

The reconstruction part 47 stores volume data in the three-dimensional image memory 29. It should be noted that in the above, volume data is generated by reconstructing DSA data that has been subjected to subtraction processing. However, without being limited to this configuration, a configuration such as the one next is also possible. For example, the image processing device 1 generates volume data that has been reconstructed from the projection data of mask images by the reconstruction part 47. Furthermore, the image processing device 1 generates volume data that has been reconstructed from contrast images by the reconstruction part 47. The subtraction processor 34 may also perform subtraction processing on the volume data of mask images and the volume data of contrast images.

<<Three-dimensional Image Memory>>

The three-dimensional image memory 29 stores the volume data received from the reconstruction part 47.

Furthermore, instead of the volume data received from the reconstruction part 47, volume data received from an external device may also be stored in the three-dimensional image memory 29. The external device is, for example, a medical diagnostic device such as an X-ray CT device, MRI device, etc. or PACS, etc. CTA (Computed Tomography Angiography) is obtained from the X-ray CT device. MRA (Magnetic Resonance Angiography), non-contrast MRA (Magnetic Resonance Angiography), etc. are obtained from the MRI device. Moreover, in case of obtaining volume data from an external device, a three-dimensional image acquiring part 36 acquires volume data from outside, for example, via a network.

Furthermore, in case of including human body information in addition to blood vessel information in the volume data from outside, the blood vessel information is extracted by employing a method such as threshold processing, range designation of pixel values or region growing, etc. by a blood vessel information-extraction part 43, and the volume data is generated. Otherwise, the blood vessel information may also be extracted to generate volume data by combining methods threshold processing, range designation of pixel values, regional growth, etc.

<<Fluoroscopic Mask Image Generation Part>>

The fluoroscopic mask image generation part 42 receives a command to generate a fluoroscopic mask image M from the control part 27. For example, this command is given when an operator conducts an operation to command the start of fluoroscopic imaging via the input device 28. That is, when receiving the command to start fluoroscopic imaging, the X-ray imaging apparatus performs imaging the subject by the X-ray imaging mechanism 10. The projection data of several frames is acquired from the imaging. The projection data is converted to digital signals and transmitted to the image processing device 1. The control part 27 of the image processing device 1 gives a command to the fluoroscopic mask image generation part 42 to generate a fluoroscopic mask image M.

The fluoroscopic mask image generation part 42 obtains projection data of several frames acquired by the fluoroscopic imaging and generates a fluoroscopic mask image M averaged for, for example, one second before being stored in the two-dimensional image memory 30.

It should be noted that upon generation of the fluoroscopic mask image M, a dynamic image generation part (not illustrated) generates a real time fluoroscopic image R. That is, a subject is subjected to imaging by the X-ray imaging apparatus using the X-ray imaging mechanism 10 at a predetermined interval. The projection data is sequentially acquired from this imaging. The sequentially acquired projection data is transmitted to the image-processing device 1. The image-processing device 1 receives the projection data and converts the projection data into digital signals. Furthermore, the control part 27 of the image processing device 1 gives a command to generate a real time fluoroscopic image R to the dynamic image generation part. The dynamic image generation part acquires the projection data that has been sequentially acquired by the fluoroscopic imaging, sequentially generates real time fluoroscopic images R, and stores the real time fluoroscopic images R in the two-dimensional image memory 30.

<<Subtraction Image Generation Part>>

When the fluoroscopic mask image M and the real time fluoroscopic image R are stored in the two-dimensional image memory 30, the control part 27 causes the subtraction image generation part 41 to generate fluoroscopic subtraction data. That is, the control part 27 reads out, from the two-dimensional image memory 30, image data or projection data of fluoroscopic mask images M and real time fluoroscopic images R that have been continuously acquired. The control part 27 transmits the data to the subtraction image generation part 41. The subtraction image generation part 41 performs subtraction processing on the real time fluoroscopic image R from the fluoroscopic mask image M to generate a fluoroscopic subtraction image by fluoroscopic imaging. It should be noted that if devices such as a guide wire, catheter, etc. have been inserted into the subject, the fluoroscopic subtraction image includes data showing the devices.

Furthermore, for a fluoroscopic subtraction image, it is preferable to perform an enhancing process for devices such as a catheter, guide wire, etc. that have been inserted into the subject. By performing the enhancing process for devices in the fluoroscopic subtraction image, a device-enhanced image D (ref. FIG. 2) is generated. For example, as an enhancing process for devices, a noise reduction process is performed. As such a noise reduction process, it is possible to adopt a median filtering process.

Furthermore, as a further enhancing process for devices, it is also possible to perform a detection process of a line component to a fluoroscopic subtraction image or a device-enhanced image D. By performing the detection process on a line component, noise components are reduced in an image without deteriorating the line component. As a result, device portions such as a guide wire, catheter, etc. can be relatively enhanced in the image.

In FIG. 7, a symbol "−" displayed between a real time fluoroscopic image and a fluoroscopic mask image means subtraction processing. Furthermore, FIG. 7 shows the steps for creating a device-enhanced image D by performing a noise-suppression process and a wire-enhancing process on a fluoroscopic subtraction image. As a guide wire-enhancing process, for example, a process exists for enhancing a high frequency component in a fluoroscopic subtraction image.

It should be noted that in some cases, these fluoroscopic subtraction images or device-enhanced images D are transmitted to the display 39 after having been composed with other images (volume rendering image V, etc.). Furthermore, sometimes a fluoroscopic subtraction image or a device-enhanced image D is transmitted to the display without being composed with other images.

<<Volume Rendering Image Generation Part>>

The volume rendering image generation part 40 reads out volume data from the three-dimensional image memory 29 and generates a volume rendering image V. That is, when an operator presses the 3D road map switch, the control part 27 of the image processing device 1 commands the volume rendering image generation part 40 to generate a volume rendering image V.

When the command to generate a volume rendering image V is received from the control part 27, the volume rendering image generation part 40 executes a process such as volume rendering, etc. to generate a volume rendering image (three-dimensional blood vessel display image). A process such as volume rendering is performed in accordance with information indicating the state of the X-ray imaging apparatus (medical image diagnosis apparatus). That is, the volume rendering image generation part 40 performs the above process so as to match the state of an X-ray imaging apparatus, for example, a state indicated by information such as the observation angle, observation field of vision, observation magnification rate, observation position, etc.

<<Image Composition Part>>

As shown in FIG. 7, the image composition part 35 cumulatively composes arbitrary combinations of a fluoroscopic subtraction image or a device-enhanced image D, a volume rendering image V, and a real time fluoroscopic image R. It should be noted that the symbol "+" displayed in FIG. 7 means composition processing. Furthermore, in FIG. 7, the symbol "k" refers to the readability of a fluoroscopic image. The "k" can be made smaller from a certain level as time elapses and can also be made smaller than 0 or an initial value after a predetermined time has elapsed. The time and readability may be appropriately set.

Furthermore, the image composition part 35 is capable of changing the composition ratio of each image via a composition ratio-changing part (not illustrated). That is, when an operation to change the composition ratio of each image is carried out by the input device 28, the composition ratio-changing part changes the transparency degree of each image (layer) according to the operation. For example, in order to grasp the movement of a guide wire, etc., when fluoroscopic imaging starts, the transparency degree of the layer of a device-enhanced image D (guide wire image, etc.) extracted in a 3D road map image S is lowered such that it is close to non-transparent. Under this condition, when the image composition part 35 composes images, the readability of devices is improved as device portions such as a guide wire, etc. are enhanced in an image. Likewise, the composition ratio-changing part is capable of relatively enhancing device portions by making the layer of other portions (real time fluoroscopic image R, etc.) in the 3D road map image S close to transparent.

In other words, the image composition part 35 composes and displays each image based on an initial value (default value) of the composition ratio of each image and, after the change in the composition ratio is made by the composition ratio-changing part, it is possible to compose each image based on the composition ratio after the change. For example, in order to grasp the movement of a subject from the volume data acquisition time until fluoroscopy starts, the ratio of the layer of a real time fluoroscopic image is increased for the display at the time when fluoroscopy starts (default value). Further, after having been confirmed that there is no movement of the subject, it is also possible to improve the readability of a device image such as guide wire, etc. or of a volume rendering image by lowering the ratio of the layer of a real time fluoroscopic image by the composition ratio-changing part.

Furthermore, the composition ratio-changing part is also capable of changing the transparency degree of the layer of each image in chronological order. For example, as the composition ratio-changing part gradually increases the degree of transparency of a real time fluoroscopic image R, the readability of a device in a 3D road map image S is increased. As the device is inserted, if the composition ratio of a portion surrounding the device (background portion) in the 3D road map image S is reduced so as to mainly display a 3D vascular image and an image in which the device is enhanced, the readability of a device, etc. is relatively improved.

That is, the composition ratio-changing part performs masking processing on the real time fluoroscopic image R. For example, the image processing device 1 performs a process of lowering the composition ratio of a real time fluoroscopic image R only with respect to a superposed portion of the real time fluoroscopic image R and a portion at which a blood vessel in a volume rendering image V is present. For example, if the composition ratio of a real time fluoroscopic image R is increased, the composition ratio of a volume rendering image V is relatively reduced. Consequently, in the volume rendering image V, the composition ratio of the portion showing blood vessels is reduced. Thereby, a situation arises such that the readability of a portion showing blood vessels in the volume rendering image deteriorates in a 3D road map image S to be displayed. Therefore, the above masking processing is performed. Thereby, even if the composition ratio of the real time fluoroscopic image R is increased, it becomes possible to avoid a situation in which the readability of the volume rendering image V is deteriorated.

Furthermore, the composition ratio-changing part starts counting the time until the composition ratio is changed from the start of fluoroscopic imaging or the generation of a device-enhanced image D. The time is preliminarily set. When the aforementioned time that has been set elapses after the time count has started, the composition ratio-changing part starts changing the composition ratio. That is, the composition ratio-changing part further multiplies the composition ratio of a real time fluoroscopic image R by a readability coefficient k. As for the changes in the composition ratio, a change curve is preliminarily set and the reduction rate of the readability coefficient k per unit of time is defined. Moreover, the composition rate-changing part starts counting the time until the change of the composition ratio is completed after the change of the composition ratio has started. The time is also preliminarily set.

As described, the composition ratio-changing part chronologically reduces the readability coefficient k to be multiplied by the composition ratio of the real time fluoroscopic image R, based on a predetermined time and a predetermined change curve, while counting the time. Consequently, a composite image is changing as the situation of the fluoroscopic imaging progresses, and the readability of a device in the image is relatively enhanced.

The timing to chronologically reduce the readability coefficient k may rely on a predetermined time elapse from the start of the fluoroscopic imaging as described above. However, an operation via the input device 28 by an operator may also be the trigger. Furthermore, it is preferable to chronologically reduce the readability coefficient k, but it is also possible to gradually reduce it via the operation of the input device 28 by the operator.

By these processes, the image composition part 35 generates a 3D road map image S. Furthermore, the background, a device-enhanced image D, a real time fluoroscopic image R, and a volume rendering image V may be composed so as to be respectively displayed in a different color. Using a LUT37, the image composition part 35 is capable of assigning a unique color to the road map portion of the composite image and changing the tonal gradation.

It should be noted that when an operator conducts intervention treatment, etc. following a command to start fluoroscopic imaging, insertion of devices, pressing the road map switch, and placing a coil sequentially in this order, the image composition part 35 behaves as below.

When the image processing device 1 receives a command to start fluoroscopic imaging via an input device 28, the image composition part 35 receives a fluoroscopic subtraction image or a device-enhanced image D, and a real time fluoroscopic image R. The image composition part 35 composes these to cause the display 39 to display.

When an operator inserts a guide wire and a catheter into a subject and gives a command to enhance these devices via the input device 28, the image composition part 35 receives a device-enhanced image D and a real time fluoroscopic image R. The composition ratio-changing part adjusts the transparency degree of these images as described above. The image composition part 35 composes these to cause the display 39 to display.

When an operator presses the road map switch, the image composition part 35 receives a device-enhanced image D, a real time fluoroscopic image R, and a volume rendering image V. The image composition part 35 composes these to cause the display 39 to display.

When the operator places a coil into an aneurysm, etc. of the subject and gives a command for reimaging as well as a command for coil extraction via the input device 28, the image composition part 35 receives a device-enhanced image D, a real time fluoroscopic image R, and a volume rendering image V. The composition ratio-changing part adjusts the transparency degree of these images as described above. The image composition part 35 composes these to cause the display 39 to display.

(Operation of Image Processing Device)

Figure 9:
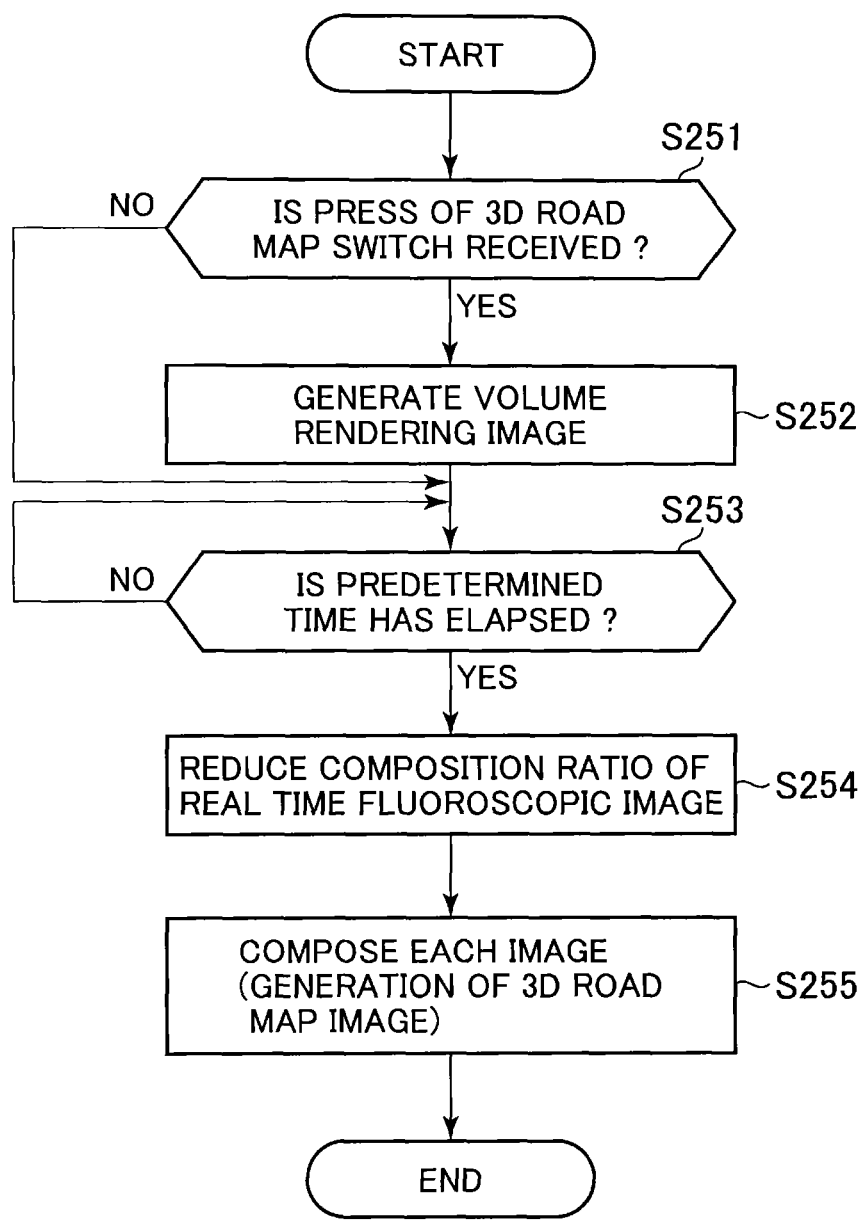
FIG. 9 is a schematic flow chart showing the steps of a process to generate a 3D road map image by the X-ray imaging apparatus of Embodiment 2.

Next, details of the processing of the aforementioned, with reference to FIG. 7, image processing device 1 are described with reference to the flow charts of FIG. 9.

<<Generation of Volume Data>>

Steps for generating volume data by the X-ray imaging apparatus in Embodiment 2 are the same as the content described in Embodiment 1 (FIG. 4/S111 to S114). Therefore, a description is omitted.

<<Fluoroscopic Imaging>>

Figure 5:
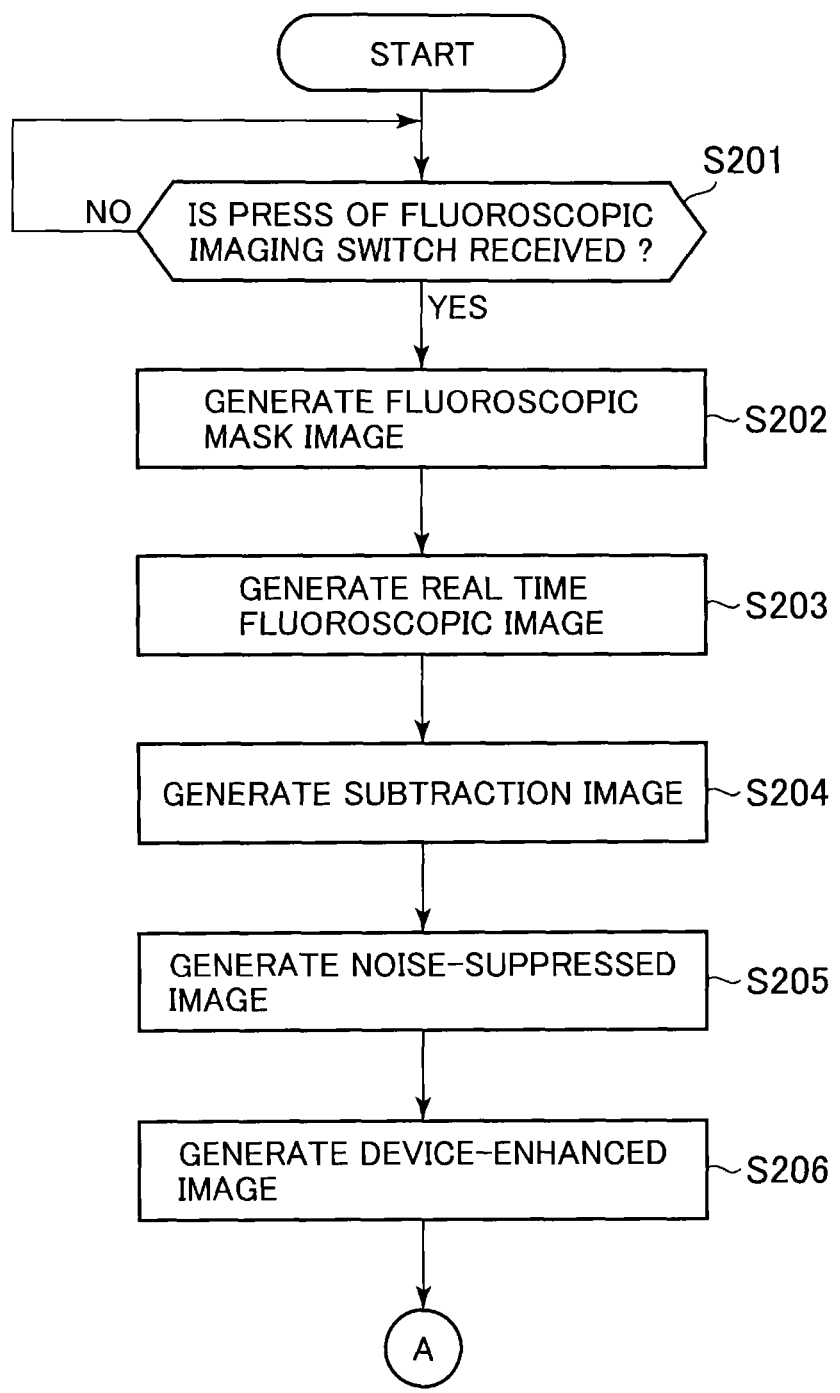
FIG. 5 is a schematic flow chart showing the steps of a process to generate a device-enhanced image by the X-ray imaging apparatus of Embodiment 1.
Figure 6:
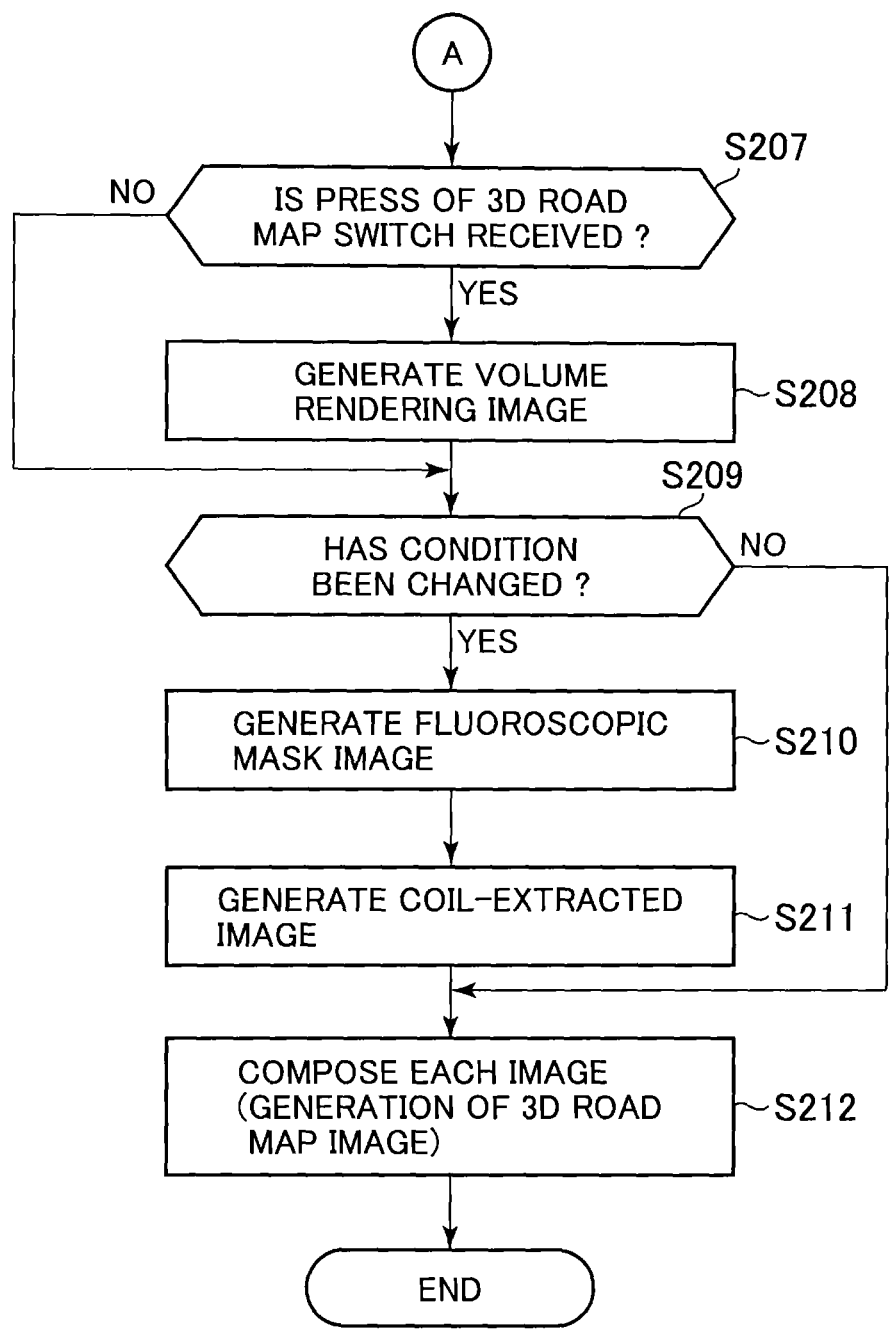
FIG. 6 is a schematic flow chart showing the steps of a process to generate a 3D road map image by the X-ray imaging apparatus of Embodiment 1.

The steps for generating a device-enhanced image D by the X-ray imaging apparatus in Embodiment 2 are the same as the content described in Embodiment 1 (FIG. 5/S201 to S206). Therefore, a description is omitted.

<<Composition of Images (Generation of 3D Roadmap Images)>>

Next, the generation step of a 3D road map image S in a treatment phase is described with reference to FIG. 9. FIG. 9 is a schematic flow chart showing the steps for the generation process of the 3D road map image S by the X-ray imaging apparatus in Embodiment 2.

(S251)

Before and after a fluoroscopic imaging switch is pressed to display a fluoroscopic subtraction image or a device-enhanced image D, a doctor inserts a guide wire, catheter, etc. in the vicinity of the aneurysm while referencing the image that is being displayed. Once the device is inserted in the vicinity of the aneurysm, the operator presses the 3D road map switch in the input device 28 for the purpose of accurately grasping the position of the aneurysm and verifying the inserted state of a coil into the aneurysm. The image processing device 1 determines whether or not the 3D road map switch has been pressed.

(S252)

When it is determined that the 3D road map switch has been pressed (S251; Yes), the image processing device 1 causes the volume rendering image generation part 40 to generate a volume rendering image V. That is, the volume rendering image generation part 40 reads out volume data from the three-dimensional image memory 29. The volume rendering image generation part 40 executes a process such as volume rendering, etc. on the volume data to generate a volume rendering image V. The process of the volume rendering, etc. is performed so as to be matched with a state indicated by information such as the observation angle, observation field of vision, observation magnification rate, observation position, etc. in the X-ray imaging apparatus.

(S253)

Once fluoroscopic imaging has started or a device-enhanced image D is generated, the image processing device 1 determines if a predetermined time has elapsed or not. The predetermined time is the time to start reducing the readability coefficient k of a real time fluoroscopic image R. The time is determined by the control part 27, etc. of the image processing device 1. It should be noted that the determination of the above condition changes is stated after step 251 or step 252 for the convenience of the statement in FIG. 9, but the timing of the determination is not limited to the pattern in FIG. 9. Furthermore, in some cases, the change in the imaging conditions is commanded via the input device 28.

(S254)

If determined by the image processing device 1 that a predetermined time has elapsed (S253; Yes), the composition ratio-changing part (not illustrated) chronologically reduces the readability coefficient k to be multiplied by the composition ratio of a real time fluoroscopic image R. The reduction rate of the coefficient k is set appropriately. Thereby, a portion of a device in a composite image composed by the image composition part 35 is relatively enhanced.

(S255)

Until the 3D road map switch is pressed (S251; No), the image composition part 35 cumulatively composes a device-enhanced image D (subtraction image) and a real time fluoroscopic image R.

When the 3D road map switch is pressed and a volume rendering image V is generated, the image composition part 35 cumulatively composes a device-enhanced image D (subtraction image), a real time fluoroscopic image R, and a volume rendering image V. Thereby, a 3D road map image S is generated.

It should be noted that the image composition part 35 is capable of composing each image and displaying the each image in a different color. Furthermore, the composition ratio of each image may be changed by the composition ratio-changing part. Due to the changes in the composition ratio of each image, the transparency degree of each image (layer) may be made different. The transparency degree of each image may be appropriately changed. That is, when a fluoroscopy starts (default value), in order to grasp the movement of the subject, the ratio of the layer of a real time fluoroscopic image R is increased to display. Further, after having been confirmed that there is no movement of the subject, it is also possible to improve the readability of a device image such as a guide wire, etc. or a volume rendering image by lowering the ratio of the layer of the real time fluoroscopic image R by the composition ratio-changing part.

The composed image data is converted into analogue by the D/A converter 38 and transmitted to the display 39. It should be noted that the analogue conversion process may sometimes be omitted depending on the display 39. Based on the analogue or digital image data received from the image processing device 1, the display 39 displays a 3D road map image S and a device-enhanced image D, etc.

As described above, Embodiment 2 is useful for devices to be used for supporting medical actions and particularly, suitable for cases in which a device operator such as a doctor visually recognizes a guide wire, catheter, coil, etc. and efficiently conducts medical actions.

[Embodiment 3]

Next, an X-ray imaging apparatus related to Embodiment 3 is described. It should be noted that in Embodiment 3, descriptions of portions overlapping with Embodiment 1 and Embodiment 2 are appropriately omitted.

In Embodiment 3, as in Embodiment 1, a coil-extracted image C is generated when conditions change in imaging during fluoroscopic imaging, which is incorporated into the generation of a 3D road map image S. Furthermore, in Embodiment 3, the composition ratio of a real time fluoroscopic image is automatically reduced as time elapses from the starting time of fluoroscopy as in Embodiment 2.

Figure 10:
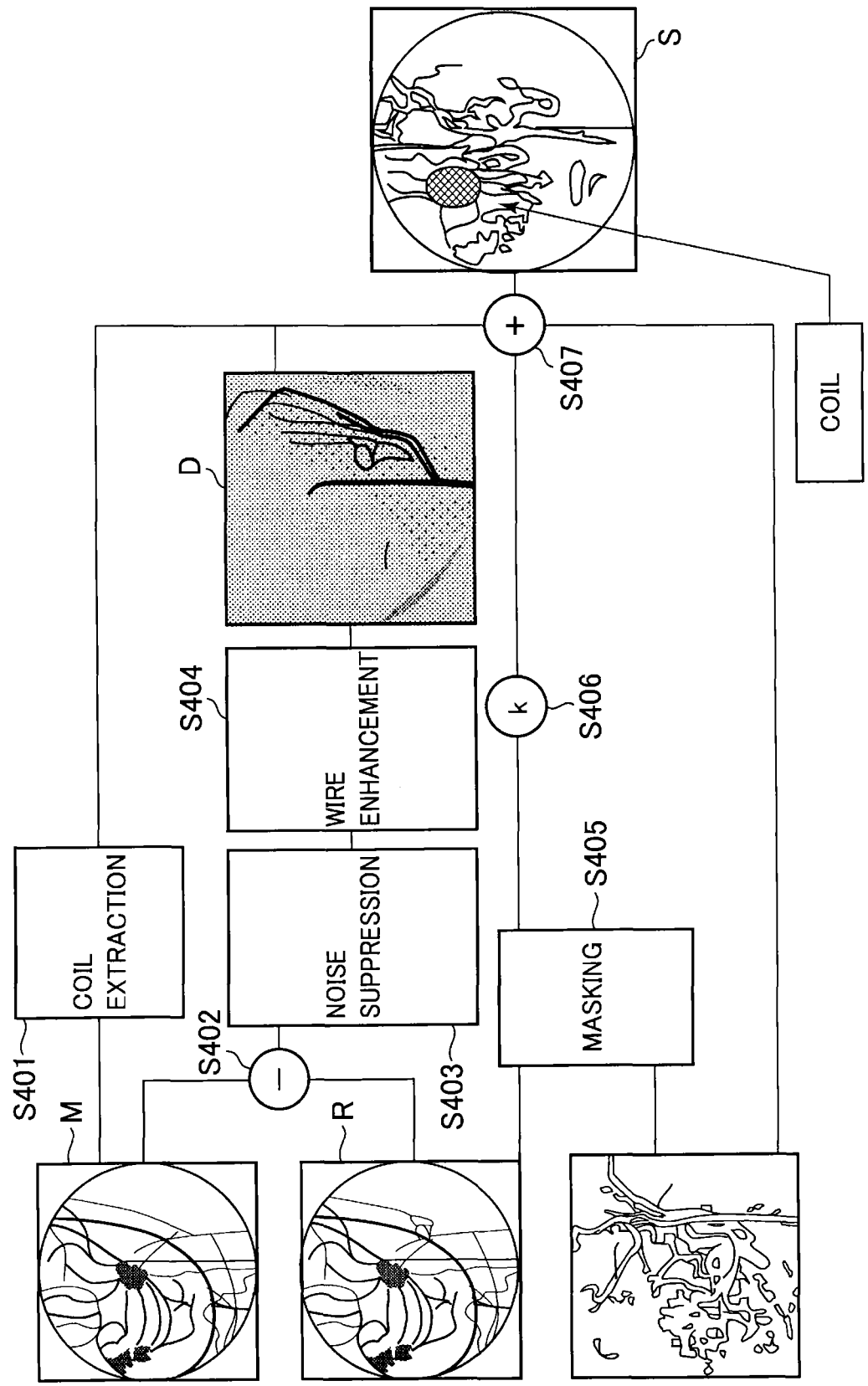
FIG. 10 is a schematic block diagram schematically showing the steps to generate a 3D road map image by the X-ray imaging apparatus of Embodiment 3.

Next, with reference to FIG. 10, the operation outline of the image processing device 1 in accordance with the condition changes in imaging or the command to regenerate a fluoroscopic mask image M is described. It should be noted that the operation is an example of coil embolization with respect to aneurysms. FIG. 10 is a schematic block diagram schematically showing the steps to generate a 3D road map image S by the X-ray imaging apparatus of Embodiment 3.

<<Generation of Coil-Extracted Images>>

As shown in FIG. 10, when there are condition changes in imaging or a command is given to regenerate a fluoroscopic mask image M, the X-ray imaging mechanism 10 reobtains a fluoroscopic mask image M as well as a real time fluoroscopic image R. Furthermore, a coil is extracted from the reobtained fluoroscopic mask image M to generate a coil-extracted image C (S401).

<<Generation of Device-Enhanced Images>>

The image processing device 1 obtains fluoroscopic subtraction data by subtraction processing the fluoroscopic mask image M and the real time fluoroscopic image R that are reobtained (S402). In FIG. 10, a symbol "−" displayed between the real time fluoroscopic image R and the fluoroscopic mask image M means subtraction processing. Furthermore, the image processing device 1 performs noise suppression processing on the fluoroscopic subtraction data (S403).

The image processing device 1 performs detection processing of a line component, etc. (enhancement of a wire) on the fluoroscopic subtraction data subjected to noise suppression processing. As a result, a device-enhanced image D in which a device such as a guide wire, etc. is relatively enhanced in the fluoroscopic image, is generated (S404).

<<Masking Processing and Adjustment of Composition Ratio>>

The image processing device 1 performs masking processing on the real time fluoroscopic image R (S405). Furthermore, the image processing device 1 chronologically reduces the composition ratio of the real time fluoroscopic image R by multiplying by a readability coefficient k with respect to the real time fluoroscopic image R such that a device in a composite image is relatively enhanced (S406).

<<3D Roadmap Image>>

Composition processing of the device-enhanced image D, and the real time fluoroscopic image R subjected to masking processing is performed by the image processing device 1 (Step S407). Furthermore, the volume rendering image V and the image data subjected to the composition processing are further subjected to composition processing to generate a 3D road map image S. Moreover, the image processing device 1 causes the display 39 to display the 3D road map image S.

The X-ray imaging apparatus in Embodiment 3 generates a coil-extracted image C as in Embodiment 1. Moreover, the X-ray imaging apparatus in Embodiment 3 chronologically changes the composition ratio of a real time fluoroscopic image R. Due to these processes, the readability of devices such as a guide wire, catheter, coil, etc. under fluoroscopic imaging is improved.

The entire configuration of the X-ray imaging apparatus in Embodiment 3 and the specific configuration of each part is the same as Embodiment 1 and Embodiment 2.

The configuration of the image-processing device 1 in Embodiment 3 is the same as Embodiment 1 and Embodiment 2. That is, the image processing device 1 in Embodiment 3 is configured comprising an A/D converter 26, a control part 27, a three-dimensional image memory 29, a two-dimensional image memory 30, a filtering part 31, an affine transformation part 32, a subtraction processor 34, an image composition part 35, a three-dimensional image acquiring part 36, an LUT (Look-up Table) 37, a volume rendering image generation part 40, a subtraction image generation part 41, a fluoroscopic mask image generation part 42, a blood vessel information extraction part 43, a reconstruction part 47, a coil image generation part 48, and a D/A converter (Digital/Analog) 38. A display 39 is connected to the image processing device 1 via the D/A convertor 38. Furthermore, an input device 28 comprising a road map switch is connected to the image processing device 1. The control part 27 controls each part of the image processing device 1. It should be noted that Embodiment 3 includes a coil image generation part 48 unlike Embodiment 2.

The specific configuration of each part of the image processing device 1 in Embodiment 3 is the same as Embodiment 1 and Embodiment 2.

(Operation of Image Processing Device)

Figure 11:
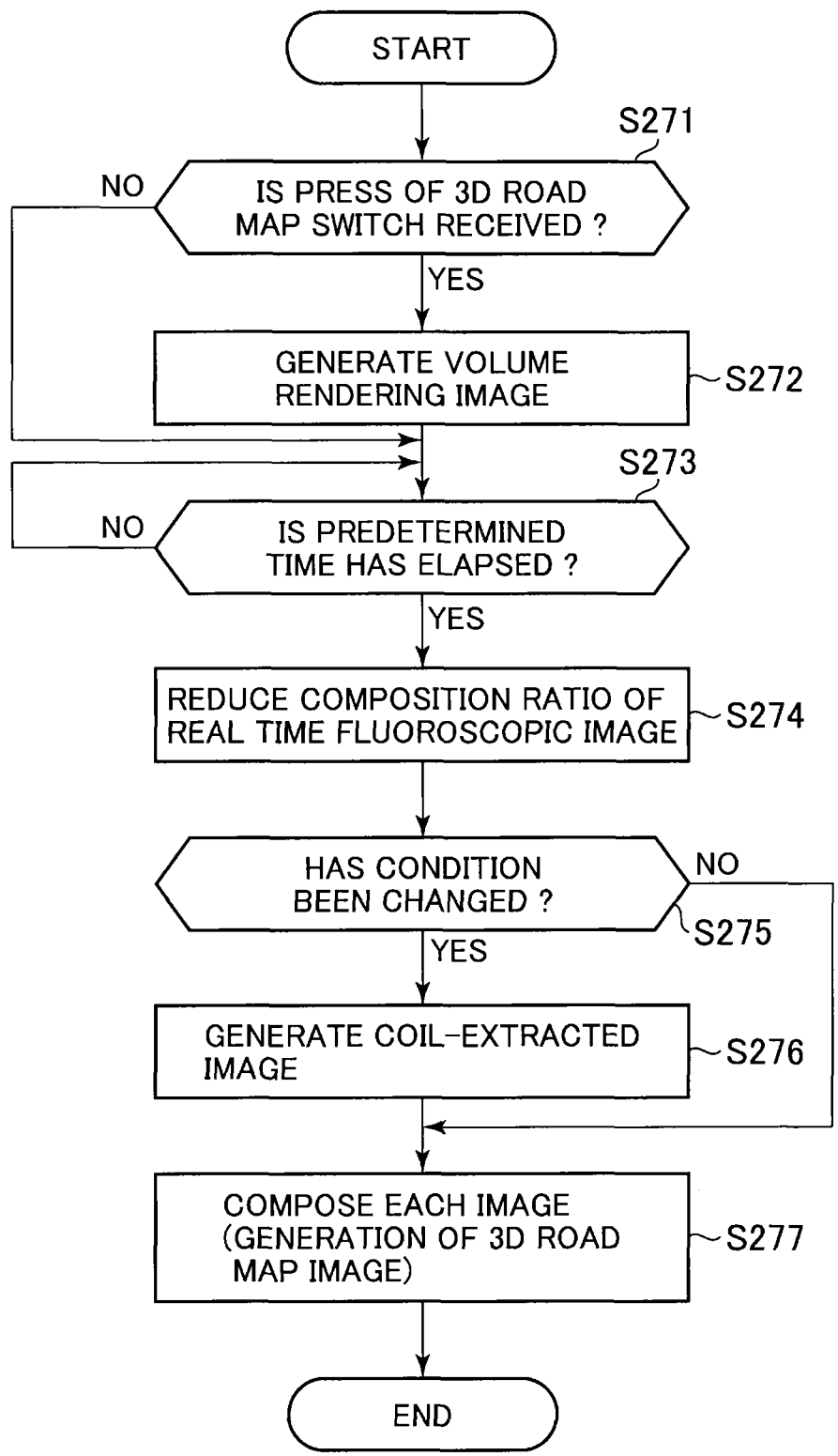
FIG. 11 is a schematic flow chart showing the steps of a process to generate a 3D road map image by the image processing device of Embodiment 2.

Next, details of the processing of the aforementioned, with reference to FIG. 10, image processing device 1 are described with reference to the flow charts of FIG. 11.

<<Generation of Volume Data>>

Steps for generating volume data by the X-ray imaging apparatus in Embodiment 3 are the same as Embodiment 1 and Embodiment 2 (ref. FIG. 4/S111 to S114).

The steps for generating a device-enhanced image D by the X-ray imaging apparatus in Embodiment 3 are the same as the content described in Embodiment 1 (FIG. 5/S201 to S206).

<<Composition of Images (Generation of 3D Roadmap Images)>>

Next, the generation step of a 3D road map image S in a treatment phase is described with reference to FIG. 11. FIG.

11 is a schematic flow chart showing the steps for the generation process of the 3D road map image S by the X-ray imaging apparatus in Embodiment 3.

(S271)

Before and after a fluoroscopic imaging switch is pressed to display a fluoroscopic subtraction image or a device-enhanced image D, a doctor inserts a guide wire, catheter, etc. in the vicinity of the aneurysm while referencing the image that is being displayed. Once the device is inserted in the vicinity of the aneurysm, the operator presses the 3D road map switch in the input device 28 for the purpose of accurately grasping the position of the aneurysm and verifying the inserted state of a coil into the aneurysm. The image processing device 1 determines whether or not the 3D road map switch has been pressed.

(S272)

When it is determined that the 3D road map switch has been pressed (S271; Yes), the image processing device 1 causes the volume rendering image generation part 40 to generate a volume rendering image V. That is, the volume rendering image generation part 40 reads out volume data from the three-dimensional image memory 29. The volume rendering image generation part 40 executes a process such as volume rendering, etc. on the volume data to generate a volume rendering image V. The process of the volume rendering, etc. is performed so as to be matched with a state indicated by information such as the observation angle, observation field of vision, observation magnification rate, observation position, etc. in the X-ray imaging apparatus.

(S273)

Once fluoroscopic imaging has started or a device-enhanced image D is generated, the image processing device 1 determines if a predetermined time has elapsed or not. The predetermined time is the time to start reducing the readability coefficient k of a real time fluoroscopic image R. The time is determined by the control part 27, etc. of the image processing device 1. It should be noted that the determination of the above condition changes is stated after step 271 or step 272 for the convenience of the statement in FIG. 11, but the timing of the determination is not limited to the pattern in FIG. 11. Furthermore, in some cases, the change in the imaging conditions is commanded via the input device 28.

(S274)

If determined by the image processing device 1 that a predetermined time has elapsed (S273; Yes), the composition ratio-changing part (not illustrated) chronologically reduces the readability coefficient k to be multiplied by the composition ratio of a real time fluoroscopic image R. The reduction rate of the coefficient k is set appropriately. Thereby, a portion of a device in a composite image composed by the image composition part 35 is relatively enhanced.

(S275)

The image processing device 1 determines, after the generation of the device-enhanced image D, whether or not the imaging conditions in the X-ray imaging apparatus (X-ray imaging mechanism 10) have changed. Changes in the imaging conditions include the observation angle, magnification rate, bed movement, patient movements, etc. The information is based on information from the X-ray imaging mechanism 10, or determined by the control part 27 etc. based on fluoroscopic images. It should be noted that the determination for changes of the above conditions is described after the step 271 to the step 274 for convenience of description in FIG. 11, the timing of determination is not limited to the pattern of FIG. 11.

(S276)

If the image processing device 1 determines that there have been changes in the imaging conditions (S275; Yes), the coil image generation part 48 performs coil extraction processing on the fluoroscopic mask image M. For example, with respect to the fluoroscopic mask image M, the coil image generation part 48 removes low frequency components by a low pass filtering process. Furthermore, the image and the fluoroscopic mask image M are subjected to subtraction processing. Moreover, by performing a threshold process, the coil image generation part 48 extracts a portion at which a coil is shown by a threshold value corresponding to the pixel value of the coil. Whereby, the coil image generation part 48 generates a coil-extracted image C.

(S277)

Until the 3D road map switch is pressed (S271; No), the image composition part 35 cumulatively composes a device-enhanced image D (subtraction image) and a real time fluoroscopic image R.

When the 3D road map switch is pressed and a volume rendering image V is generated, the image composition part 35 cumulatively composes a device-enhanced image D (subtraction image), a real time fluoroscopic image R, and a volume rendering image V. Thereby, a 3D road map image S is generated.

Once the coil-extracted image C is generated (S275; Yes), the image composition part 35 cumulatively composes a device-enhanced image D (subtraction image), a real time fluoroscopic image R, a volume rendering image V, and a coil-extracted image C. Thereby, a 3D road map image S is generated.

It should be noted that the image composition part 35 is capable of composing each image and displaying the each image in a different color. Furthermore, the composition ratio of each image may be changed by the composition ratio-changing part. Due to the changes in the composition ratio of each image, the transparency degree of each image (layer) may be made different. The transparency degree of each image may be appropriately changed. That is, when a fluoroscopy starts (default value), in order to grasp the movement of the subject, the ratio of the layer of a real time fluoroscopic image R is increased to display. Further, after having been confirmed that there is no movement of the subject, it is also possible to improve the readability of a device image such as a guide wire, etc. or a volume rendering image by lowering the ratio of the layer of the real time fluoroscopic image R by the composition ratio-changing part.

The composed image data is converted into analogue by the D/A converter 38 and transmitted to the display 39. It should be noted that the analogue conversion process may sometimes be omitted depending on the display 39. Based on the analogue or digital image data received from the image processing device 1, the display 39 displays a 3D road map image S and a device-enhanced image D, etc.

As described above, Embodiment 3 is useful for devices to be used for supporting medical actions and particularly, suitable for cases in which a device operator such as a doctor visually recognizes a guide wire, catheter, coil, etc. and efficiently conducts medical actions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising:
a volume rendering image generation part that generates, from volume data, a volume rendering image that represents blood vessel information inside a subject;
a mask image-storage that stores fluoroscopic mask images;
a real time fluoroscopic image generation part that acquires real time fluoroscopic images for each chronological sequence accompanying device insertion;
a subtraction image generation part that generates a subtraction image by subtraction processing on the fluoroscopic mask image stored in said mask image storage and the real time fluoroscopic image acquired for each chronological sequence;
a coil image generation part that generates a coil image from the fluoroscopic mask image; and
an image composition part that generates a composite image of the volume rendering image, the subtraction image, and the coil image.

2. The medical image diagnosis apparatus according to claim 1, wherein said coil image generation part extracts a coil image and performs a low pass filter process on the fluoroscopic mask image, the subtraction image generation part performs a subtraction process on the fluoroscopic mask image and a filtering image.

3. The medical image diagnosis apparatus according to claim 1, wherein the image composition part cause the coil image, the subtraction image and the volume rendering image to be displayed such that one or two of these images is given a color with hue or saturation that is different from the rest of these images.

4. The medical image diagnosis apparatus according to claim 1, wherein the subtraction image generation part performs noise reduction process on the image generated by performing subtraction processing on the fluoroscopic mask image from the real time fluoroscopic image.

5. The medical image diagnosis apparatus according to claim 4, wherein said noise reduction process is median filtering process.

6. The medical image diagnosis apparatus according to claim 1, wherein the subtraction image generation part performs detection process of a line component on the image generated by performing subtraction processing on the fluoroscopic mask image from the real time fluoroscopic image.

7. The medical image diagnosis apparatus according to claim 1, wherein the image composition part comprises a composition ratio-changing part that changes the composition ratio of each image of the volume rendering image, the subtraction image that is generated by subtraction processing on the real time fluoroscopic image and the fluoroscopic mask image, and the coil image.

8. The medical image diagnosis apparatus according to claim 7, wherein image composition part composes and displays each image based on the composition ratio that is preliminarily set, and after the composition ratio is changed by said composition ratio-changing part, composes each image based on the changed composition ratio.

* * * * *